(12) United States Patent
Fortin

(10) Patent No.: US 8,222,295 B2
(45) Date of Patent: *Jul. 17, 2012

(54) COMPOSITIONS COMPRISING POLYUNSATURATED FATTY ACID MONOGLYCERIDES OR DERIVATIVES THEREOF AND USES THEREOF

(75) Inventor: Samuel Fortin, Ste-Luce (CA)

(73) Assignee: Centre de Recherche sur les Biotechnologies Marines, Rimouski (CA)

( * ) Notice: Subject to any disclaimer, the term of this patent is extended or adjusted under 35 U.S.C. 154(b) by 227 days.

This patent is subject to a terminal disclaimer.

(21) Appl. No.: 12/535,990

(22) Filed: Aug. 5, 2009

(65) Prior Publication Data

US 2009/0291102 A1 Nov. 26, 2009

Related U.S. Application Data

(63) Continuation-in-part of application No. PCT/CA2008/000530, filed on Mar. 19, 2008.

(60) Provisional application No. 60/895,795, filed on Mar. 20, 2007.

(51) Int. Cl.
A61K 31/22 (2006.01)
A61K 31/16 (2006.01)
A61K 31/10 (2006.01)
A61K 36/00 (2006.01)
A61K 36/02 (2006.01)
A23D 9/00 (2006.01)

(52) U.S. Cl. ........ 514/549; 514/627; 514/713; 514/560; 554/224; 424/725; 424/756; 424/195.17

(58) Field of Classification Search ................. 514/560, 514/549, 627
See application file for complete search history.

(56) References Cited

U.S. PATENT DOCUMENTS

| 6,180,671 B1 | 1/2001 | Freedman et al. |
| 6,552,081 B1 | 4/2003 | Freedman et al. |
| 7,138,431 B1* | 11/2006 | Chilton ................ 514/558 |
| 7,981,915 B2 | 7/2011 | Freedman |
| 2002/0188024 A1* | 12/2002 | Chilton et al. ............ 514/560 |
| 2004/0214799 A1 | 10/2004 | Mukai et al. |
| 2009/0292019 A1 | 11/2009 | Fortin |
| 2010/0160261 A1 | 6/2010 | Fortin |
| 2010/0196496 A1 | 8/2010 | Fortin |

FOREIGN PATENT DOCUMENTS

| WO | 02064166 | 8/2002 |
| WO | 02089787 | 11/2002 |
| WO | 02096408 | 12/2002 |
| WO | 2004024136 | 3/2004 |
| WO | 2004064716 | 8/2004 |
| WO | 2006/117668 | 11/2006 |

(Continued)

OTHER PUBLICATIONS

Rosu et al., CAS: 129:105951, 1998.*

(Continued)

Primary Examiner — Yate K Cutliff
(74) Attorney, Agent, or Firm — Bereskin & Parr LLP/S.E.N.C.R.L., s.r.l.

(57) ABSTRACT

There are provided various compounds and compositions comprising polyunsaturated fatty acid monoglycerides and derivatives thereof. These compounds and compositions can be useful as cancer chemopreventive agents. They can also be useful for enhancing solubility of various active agents and enhancing their bioavailability.

21 Claims, 9 Drawing Sheets

In vitro assay of a mixture comprising composition 1 and purified curcumin on human colon cancer cell line (HCT15)

FOREIGN PATENT DOCUMENTS

WO 2008036353 3/2008

OTHER PUBLICATIONS

Watanabe et al. CAS: 139:350107, 2003.*

Aggarwal et al., Chapter 10, Curcumin-Biologican and medicinal Properties, 2007, Medicinal and Aromatic Plants—Industrial Profiles, Turmeric, 45, 297-368.*

Monks, A., "Feasibility of a High-Flux Anticancer Drug Screen Using a Diverse Panel of Cultured Human Tumor Cell Lines", J Natl Cancer Inst, Jun. 5, 1991, 757-766, vol. 83, No. 11.

Rubinstein, L.V., "Comparison of In Vitro Anticancer-Drug-Screening Data Generated with a Tetrazolium Assay Versus a Protein Assay Against a Diverse Panel of Human Tumor Cell Lines", J Natl Cancer Inst, Jul. 4, 1990, 1113-1118, vol. 82, No. 13.

Skehan, P., "New Colorimetric Cytotoxicity Assay for Anticancer-Drug Screening", J Natl Cancer Inst, Jul. 4, 1990, 1107-1112, vol. 82, No. 13.

Rose, D.P., "Omega-3 fatty acids as cancer chemopreventive agents", Pharmacology & Therapeutics, 1999, 217-244, 83.

Ohta et al., "Action of a New Mammalian DNA Polymerase Inhibitor, Sulfoquinovosyldiacylglycerol", Biol. Pharm. Bull., 1999, 111-116, 22(2).

Pacetti et al., "High performance liquid chromatography-tandem mass spectrometry of phospholipid molecular species in eggs from hens fed diets enriched in seal blubber oil", Journal of Chromatography A, 2005, 66-73, 1097.

Schaaf et al., "Polyunsaturated monoglycerides and a pregnadiene in defensive glands of the water beetle *Agabus affinis*". Department of Aimal Ecology II, University of Bayreuth, Bayreuth, Germany. Lipids (2000), 35(5), 543-550.

Vandevoorde et al. Influence of the degree of unsaturation of the acyl side chain upon the interaction of analogues of 1-arachidonoylglycerol with monoacyglycerol lipase abd fatty acid amide hydrolase. Department of Pharmacology and Clinical Neuroscience, Umea University, Umea, Swed. Biochemical and Biophysical Research Communications (2005), 337(1), 104-109. Publisher: Elsevier.

Akoh, Casimir C., Lipase-catalyzed synthesis of partial glyceride. Dep. Food Sci. Technol., Univ. Georgia, Athens, GA, USA. Biotechnoloy Letters (1993), 15(9), 949-954.

An English abstract of JP2000044588. Yagi et al. Novel monoacylglycosyl monoacylglycerols for surfactants. (Agency of Industrial Sciences and Technology, Japan) Jpn. Kokai Tokkyo Koho (2000), 7 pp. CODEN.

Rosu et al., "Enzymic synthesis of glycerides from DHA-enriched PUFA ethyl ester by glycerolysis under vacuum". Graduate school of Bio- and Agro-Sciences, Laboratory of Molecular Biotechnology, Nagoya University, Nagoya Japan. Journal of Molecular Catalysis B. Enzymatic (1988), 4(4), 191-198.

Yamane et al. "Mutiple intensified performance of an enzyme-catalyzed reaction in organic medium". Laboratory of Molecular Biotechnology Graduates School of Bio- and Agro-Sciences, Nagoya University, Nagoya, Japan. Annals of the New York Academy of Sciences (1988), 864 (Enzyme Engineering XIV), 171-179.

Ando et al., "Reinvestigation of positional distribution of fatty acids in docosahexaenoic acid-rich fish oil triacyl-sn-glycerols". Deparment of Marine Bioresources Chenmistry, Faculty of Fisheries, Hokkaido Universit, Hakodate, Japan. Lipids (2000), 35(5), 579-582.

Kawashima et al., "Enzymatic synthesis of high-purity structured lipids with caprylic acid at 1,3-positions and polyunsaturated fatty acid at 2-positin". Sonoda Wowen's Junior College, Hyogo, Japan. Journal of the American Oil Chemists' Society (2001) 78(6), 611-616.

Watanabe et al. "n-3 Polyunsaturated fatty acid (PUFA) deficiency elevates and n-3 PUFA enrichment reduces brain 2-arachidonoyglycerol level in mice" Institute of Natural Medicine, Department of Clinical Application, Toyama Medical and Pharmaceutical University, Toyama, Japan. Prostaglandins Leukotrienes and Essential Fatty Acids (2003), 69(1), 51-59.

Watanabe et al., "Chemical signals involved in larval metamorphosis in Hydroides Ezoensis (Serpulidae; Polychaeta). Part II: isolation and identification of a new monoacyl Glycerol from adult tube clumps as a metamorphosis-including substance". Department of Applied Biological Chemistry, Faculty of Agricultur, Shizuoka University, Shizuoka, Japan. Journal of Marine Biotechnology (1998), 61(1), 11-15.

A partial English translation of Tanaka et al., Preparative separation of acylglycerol by cebtrifugal partition chromatography (CPC). Tsukuba Res. Lab., Nippon Oil and Fats Co., Ltd., Tsukuba, Japan. Yukagaku (1992), 41(1), 23-7.

Feng Li et al., "Biosynthesis of Docosahexaenoate-Containing Glycerolipid Molecular Species in the Retina" Journal of Molecular Neuroscience (2001), vol. 16, 206-214.

An English abstract of JP7149786 of Yazama et al., "Glyceroglycolipid and Carcinogenic Promoter Inhibitor", published on Jun. 13, 1995.

Zerouga et al., "Synthesis of a Novel Phosphatidylcholine Conjugated to Docosahexaenoic Acid and Methotrexate that Inhibits Cell Proliferation" Anti-Cancer Drugs (2002), 13, pp. 301-311.

An English Abstract of JP 02131418 of Okazaki et al., "Comparison of Enhanced and Routine Methods for Measuring Ambient Low-Level Sulfur Dioxide". (Sansei Pharmaceutical Co., Ltd., Japan.) Jpn. Kokai Tokkyo Koho (1980), 7 pp.

An abstract of Myrdal et al., "Solubilization of Drugs in Aqueous Media" Department of pharmacy Practice and Science, College of Pharmacy, The University of Arizona, Encyclopedia of pharmaceutical technology, published on Oct. 2, 2006.

An abstract of Rohan et al., "Dietary factors and survival from breast cancer", National Cancer Institute of Canada (NCIC) Epidemiology Unit, University of Toronto, Nutr Cancer 1993,20(2) 167-77.

Kafrawy et al., "Docosahexaenoic acid in phosphatidylcholine mediates cytotoxacity more effectively than other $\omega$-3 and $\omega$-6 fatty acids", Department of Biology, Indiana University, Cancer Letters 132(1998) 23-29.

Beharry et al., "Long-term docosahexaenoic acid therapy in a congenic murine model of cystic fibrosis", Am J Physiol Gastrointest Liver Physiol 292:G839-G848, Nov. 9, 2006.

C. R. Martin et al., "The safety and efficacy of oral docosahexaenoic acid supplementation for the treatment of primary sclerosing cholangitis—a pilot study", Aliment Pharmacol Ther, Nov. 30, 2011; 35: 255-265.

Freedman et al., "Fatty acids in cystic fibrosis", Curr Opin Pulm Med 2000, 6:530-532.

Kawashima et al., "Inhibition of Rat Liver Microsomal Desaturases by Curcumin and Related Compounds", Biosci. Biotech. Biochem., 60(1), pp. 108-110, 1996.

Shimizu et al., "Sesamin is a Potent and Specific Inhibitor of $\Delta 5$ Desaturase in Polyunsaturated Fatty Acid Biosynthesis", LIPIDS, vol. 26, No. 7, pp. 512-516, 1991.

Nakano et al., "Inhibitory Effects of Capsaicinoids on Fatty Acid Desaturation in a Rat Liver Cell Line", Biosci. Biotech. Biochem., 65(8), pp. 1859-1863, 2001.

Kawashima et al., "Nicardipine and Nifedipine Inhibit Fatty Acid Desaturases in Rat Liver Microsomes", Biosci. Biotech. Biochem., 60(10), pp. 1672-1676, 1996.

Kawashima et al., "Inhibitory effects of alkyl gallate and its derivatives on fatty acid desaturation", Biochimica et Biophysica Acta 1299, pp. 34-38, 1996.

Chau et al., "Monoglyceride and diglyceride lipases from human platelet microsomes", Biochimica et Biophysical Acta, 963, pp. 436-444, 1998.

* cited by examiner

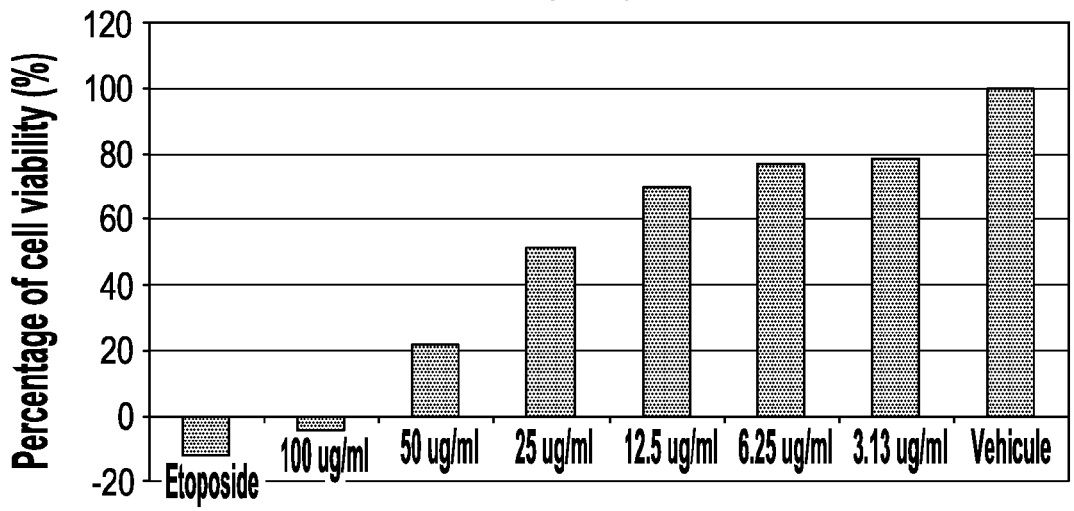
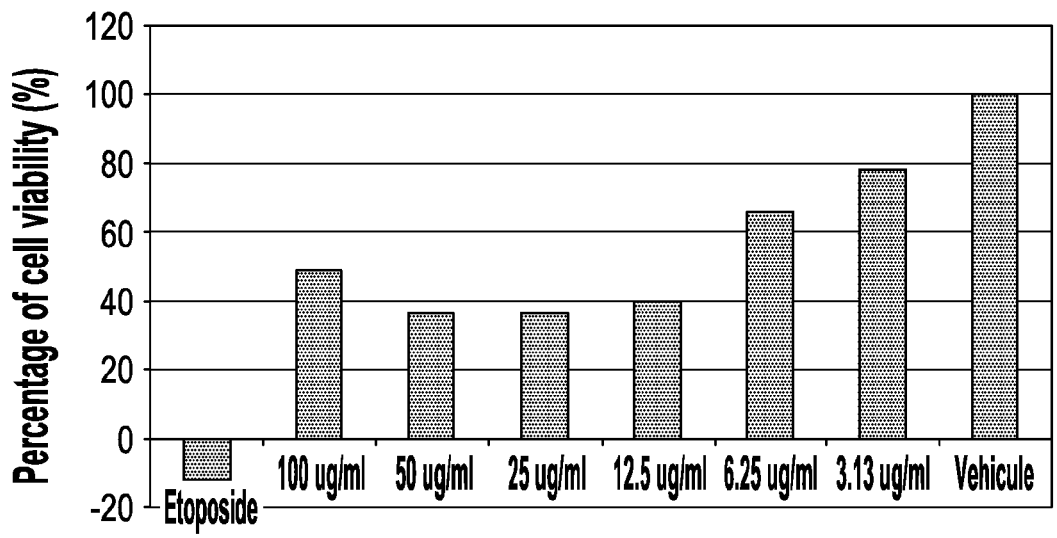

COMPOSITIONS COMPRISING POLYUNSATURATED FATTY ACID MONOGLYCERIDES OR DERIVATIVES THEREOF AND USES THEREOF

CROSS-REFERENCE TO RELATED APPLICATIONS

The present application is a continuation-in-part of PCT international patent application No. PCT/CA2008/000530 filed on Mar. 19, 2008, which claims priority on U.S. provisional application No. 60/895,795 filed on Mar. 20, 2007. These applications are incorporated herein by reference in their entirety.

FIELD OF THE DISCLOSURE

The present disclosure relates to the field of medicinal chemistry. More particularly, it relates to polyunsaturated fatty acid monoglyceride compounds and derivatives thereof. It also relates to compositions which comprise such compounds. There is also provided a method for enhancing the bioavailability of an active agent and a method for enhancing solubility of such an active agent.

BACKGROUND OF THE DISCLOSURE

The primary targets for any dosage formulation is to deliver the necessary concentration of an active drug to the site of action to elicit the desired therapeutic response and to maintain an effective concentration of the drug for a sufficient period to achieve efficacious treatment. Oral administration is generally preferred but is frequently dependent upon the bioavailability of the active form of the drug, i.e., the rate and extent that the active form of the drug appears from the dosage form in the systemic circulation. Bioavailability is affected by the drug's physical chemical properties, such as pKa, water solubility, oil solubility and stability, as well as its absorption, distribution, metabolism and excretion. It is well known that water insoluble drugs are not generally available for absorption through intestinal lumin and oil insoluble drugs are generally unable to pass across intestine cell membranes into systemic circulation (S. H. Yalkowsky, "DRUGS AND THE PHARMACEUTICAL SCIENCES: TECHNIQUES OF SOLUBILIZATION OF DRUGS," Marcel Dekker, Inc., Vol. 12, 1981). Proper formulations can improve the bioavailability of a drug.

SUMMARY OF THE DISCLOSURE

According to one aspect there are provided compounds of formulas (I), (II), (III), and (IV):

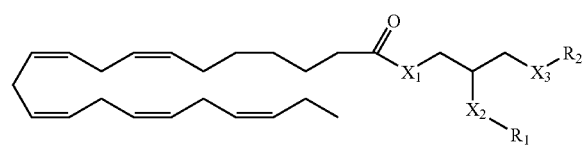

I

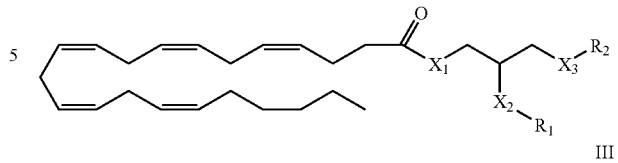

II

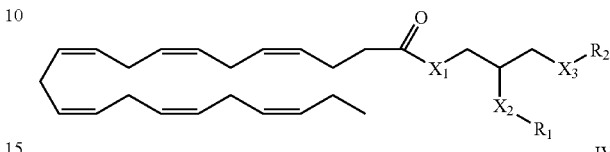

III

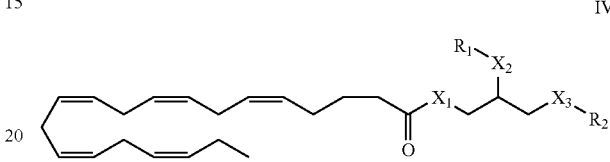

IV wherein
$X_1$ is O, NH, or S;
$X_2$ is O, NH, or S;
$X_3$ is O, NH, or S;
$R_1$ and $R_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$amino acid wherein the amino acid is connected through its alpha carbon atom, —(CH$_2$)$_n$peptide wherein the peptide is connected through the alpha carbon atom of one of its amino acids, —CH$_2$OR$_5$, —C(O)R$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate or $R_1$ and $R_2$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

$R_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$amino acid wherein the amino acid is connected to the compound through its alpha carbon atom, a —(CH$_2$)$_n$peptide wherein the peptide is connected to the compound through the alpha carbon atom of one of its amino acids, a sugar or a sugar phosphate; and n is an integer having a value of 0, 1, 2, 3, or 4, and pharmaceutically acceptable salts thereof.

According to another aspect there are provided compounds of formulas (V), (VI), (VII), (VIII), (IX), (X), (XI), (XII), (XIII), (XIV) or (XV):

V
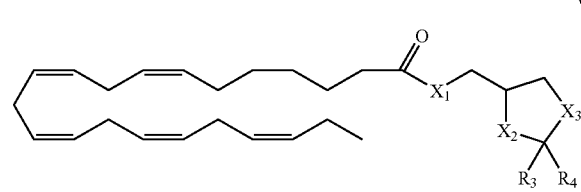

VI
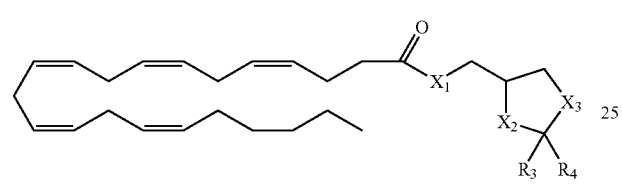

VII
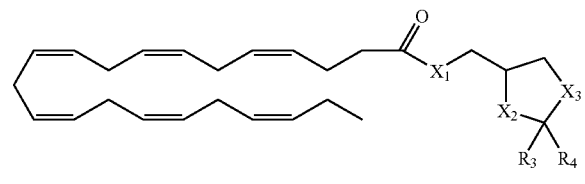

VIII
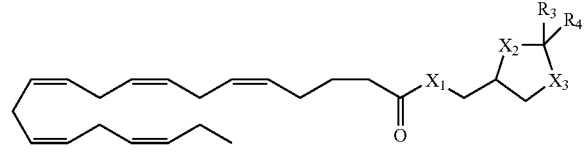

IX
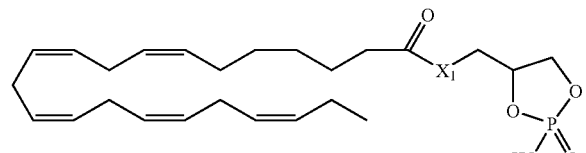

X
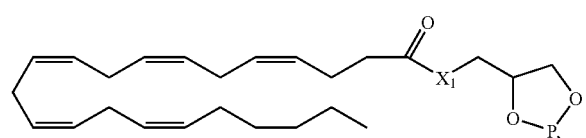

XI
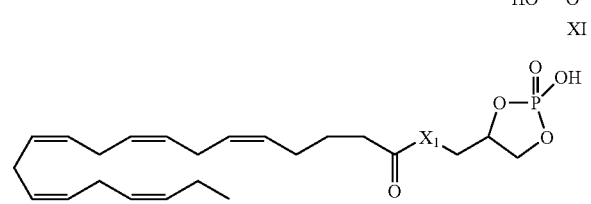

XII
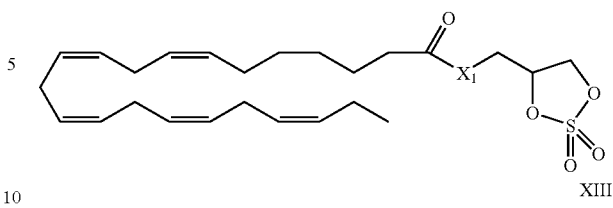

XIII
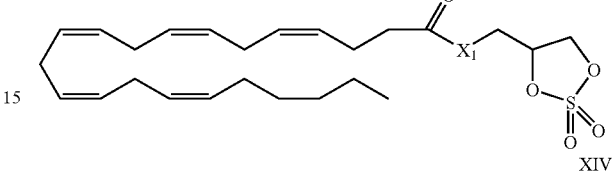

XIV
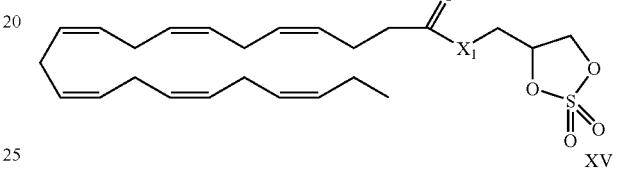

XV
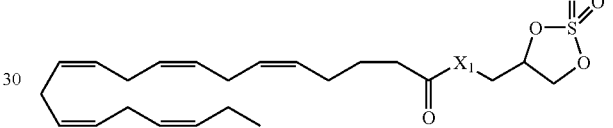

$X_1$ is O, NH, or S;
$X_2$ is O, NH, or S;
$X_3$ is O, NH, or S;

$R_3$ and $R_4$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$amino acid wherein the amino acid is connected through its alpha carbon atom, —(CH$_2$)$_n$peptide wherein the peptide is connected through the alpha carbon atom of one of its amino acids, —CH$_2$OR$_5$, —C(O)R$_4$, —C(O)OR$_4$, —C(O)NR$_4$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate, or $R_3$ and $R_4$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

$R_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —$(CH_2)_n$amino acid wherein the amino acid is connected to the compound through its alpha carbon atom, a —$(CH_2)_n$peptide wherein the peptide is connected to the compound through the alpha carbon atom of one of its amino acids, a sugar or a sugar phosphate; and n is an integer having a value of 0, 1, 2, 3, or 4;
and pharmaceutically acceptable salts thereof.

The previously mentioned compounds can be used separately or in a mixture (or composition) of at least two of them (for example 2, 3, 4, 5 or 6 of them). Thus, the present disclosure also includes compositions comprising at least two compounds of the present disclosure, According to another aspect, there is provided a composition comprising at least one compound chosen from compounds of formulas I, II, III, IV, V, VI, VII, VIII, IX, X, XI, XII, XIII, XIV, and XV; and at least one active agent.

According to another aspect, there is provided a method for solubilizing a lipophilic active agent. The method comprises mixing the lipophilic active agent with at least one compound chosen from compounds of formulas I, II, III, IV, V, VI, VII, VIII, IX, X, XI, XII, XIII, XIV, and XV. The method can further comprise mixing a lipid with the at least one compound and the lipophilic active agent.

According to another aspect, there is provided a method for enhancing the solubility of at least one active agent in a lipid or a lipid formulation. The method comprises mixing the at least one active agent, and at least one compound chosen from compounds of formulas I, II, III, IV, V, VI, VII, VIII, IX, X, XI, XII, XIII, XIV, and XV. The method can comprise mixing together the at least one active agent and the at least one compound so as to obtain a composition and then, mixing the lipid and the composition or the method can comprise mixing together the lipid and the at least one compound so as to obtain a composition and then, mixing the at least one active agent and the composition. For example, the lipid can be chosen from compounds of formulas I, II, III, IV, V, VI, VII, VIII, IX, X, XI, XII, XIII, XIV, and XV or the lipid formulation can comprise at least one compound chosen from compounds of formulas I, II, III, IV, V, VI, VII, VIII, IX, X, XI, XII, XIII, XIV, and XV.

According to another aspect, there is provided a method for enhancing bioavailability of at least one active agent. The method comprises mixing the at least one active agent with at least one compound chosen from compounds of formulas I, II, III, IV, V, VI, VII, VIII, IX, X, XI, XII, XIII, XIV, and XV.

For example, the compounds and compositions of the present disclosure can be used for treating cancer (for example breast cancer, lung cancer, prostate cancer, colon cancer).

For example, the compounds and compositions of the present disclosure can be used for enhancing bioavailability of at least one active agent.

According to another aspect, there is provided a method for inhibiting tumor growth, inhibiting tumor cell proliferation, or reducing tumor growth, in vitro or in vivo. The method comprises contacting the tumor with an effective amount of at least one compound or composition as previously described.

According to another aspect, there is provided a method for chemopreventing cancer comprising administering to a subject an effective amount of at least one compound or composition as previously defined. Such a cancer can be lung cancer, prostate cancer, breast cancer, or colon cancer.

According to another aspect, there is provided a method for reducing tumor growth in a subject comprising administering to the subject an effective amount of at least one compound or composition as previously defined.

According to another aspect there is provided a method for treating cancer (for example breast cancer, lung cancer, prostate cancer, colon cancer) comprising administering to the subject in need thereof an effective amount of at least one compound chosen from compounds of formulas I, II, III, IV, V, VI, VII, VIII, IX, X, XI, XII, XIII, XIV, and XV.

According to another aspect there is provided a method for treating cancer (for example breast cancer, lung cancer, prostate cancer, colon cancer) comprising administering to the subject in need thereof an effective amount of at least one active agent and an effective amount of at least one compound of the present disclosure. For example, a composition comprising an effective amount of the at least one active agent and an effective amount of at least one compound of the present disclosure can be administered. Alternatively, the effective amount of the at least one active agent and the effective amount of the at least one compound can be administered separately. For example, the active agent can be curcumin.

According to another aspect there is provided a method for inhibiting tumor growth, inhibiting tumor cell proliferation, or reducing tumor growth, in vitro or in vivo, comprising administering an effective amount of at least one active agent and an effective amount of at least one compound of the present disclosure. For example, a composition comprising an effective amount of the at least one active agent and an effective amount of at least one compound of the present disclosure can be administered. Alternatively, the effective amount of the at least one active agent and the effective amount of the at least one compound can be administered separately.

According to another aspect, there is provided a method for enhancing bioavailability of at least one active agent. The method comprises mixing the at least one active agent with at least one compound of the present disclosure.

According to another aspect, there is provided a method for enhancing bioavailability of at least one active agent. The method comprises administering to a subject an effective amount of the at least one active agent and an effective amount of at least one compound of the present disclosure. For example, a composition comprising an effective amount of the at least one active agent and an effective amount of at least one compound of the present disclosure can be administered. Alternatively, the effective amount of the at least one active agent and the effective amount of the at least one compound can be administered separately.

According to another aspect, there is provided a method for enhancing bioavailability of at least one lipophilic active agent, natural product or natural crude extract. The method comprises administering to a subject an effective amount of the at least one lipophilic active agent, natural product or natural crude extract and an effective amount of at least one compound of the present disclosure. For example, a composition comprising an effective amount of the at least one lipophilic active agent, natural product or natural crude extract and an effective amount of the at least one compound of the present disclosure can be administered. Alternatively, the effective amount of the at least one lipophilic active agent, natural product or natural crude extract and the effective amount of the at least one compound can be administered separately.

According to another aspect, there is provided a method for enhancing bioavailability of at least one active agent present in at least one oil. The method comprises administering to a subject an effective amount of the at least one oil and an effective amount of at least one compound of the present disclosure. For example, a composition comprising an effective amount of the at least one oil and an effective amount of at least one compound of the present disclosure can be administered. Alternatively, the effective amount of the at least one oil and the effective amount of the at least one compound can be administered separately.

It was found that the compounds and compositions previously mentioned can be useful as bioavailability enhancers of various types of active agents.

It was also found that the compounds and compositions previously mentioned can enhance the solubility of an active agent such as a lipophillic active agent. It was observed that active agents can be more easily solubilized in the compounds and compositions previously defined than in the usual lipids or lipid formulations. Thus, the active agents that need to be dissolved in a lipid or a lipid formulation can be dissolved in the compounds or compositions as those previously defined instead than in other conventional lipids or lipid formulations. Alternatively, such active agents can be mixed with at least one compound or composition as previously defined in order to obtain another composition and then the other composition can be dissolved in a lipid or a lipid formulation. In such a case, the overall solubility of the active agent in the lipid or lipid formulation is enhanced.

According to another aspect, there is provided a method for treating an inflammatory disease comprising administering to a subject in need thereof an effective amount of at least one active agent and an effective amount of at least one compound of the present disclosure. For example, a composition comprising an effective amount of the at least one active agent and an effective amount of at least one compound of the present disclosure can be administered. Alternatively, the effective amount of the at least one active agent and the effective amount of the at least one compound can be administered separately.

BRIEF DESCRIPTION OF THE FIGURES

Further features and advantages will become more readily apparent from the following description of specific embodiments as illustrated by way of examples in the appended figures wherein:

FIG. 1 represents an in vitro assay of a composition according to an example, wherein the assay was carried out on A549 human cancer cell line;

FIG. 2 represents an in vitro assay of a composition according to another example, wherein the assay was carried out on A549 human cancer cell line;

DETAILED DESCRIPTION OF THE DISCLOSURE

Figure 3:
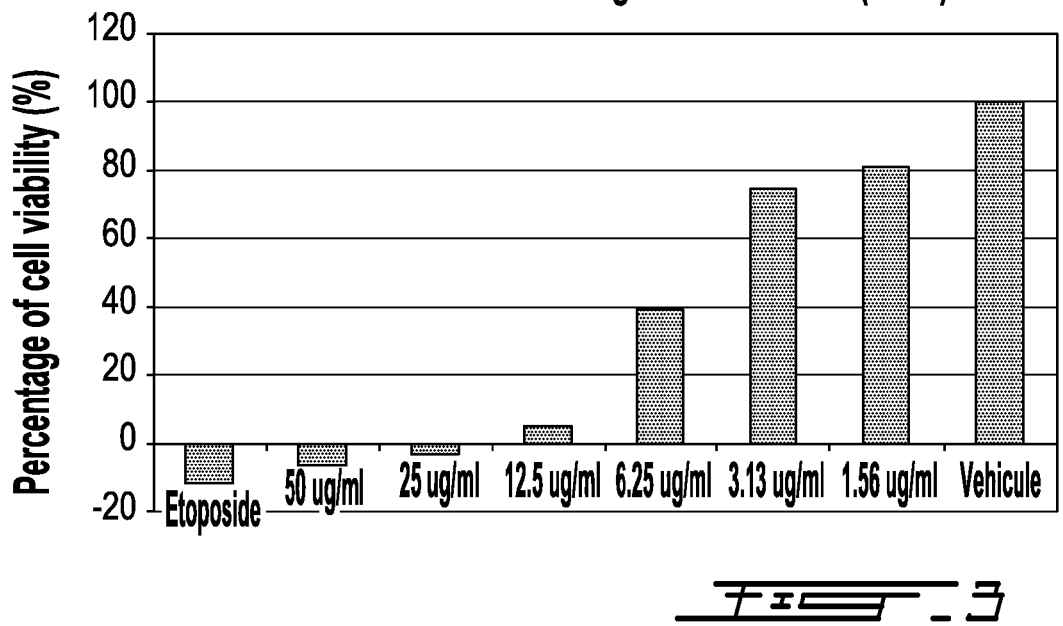
FIG. 3 represents an in vitro assay of a composition according to another example, wherein the assay was carried out on A549 human cancer cell line.

Further features and advantages of the previously-mentioned compounds will become more readily apparent from the following description of non-limiting examples.

The compounds and compositions of the present disclosure can also be effective so as to enhance solubility of various active agents. They can also be used as a emulsifier alone, emulsifier in a self-emulsifying drug delivery systems (SEDDS), self-microemulsifying drug delivery systems (SMEDDS) and selfemulsifying oil formulations (SEOF) for improved oral delivery of a lipophilic active agent, natural product or natural crude extract. They can also be used in combination with a 1-monoglyceride, 2-monoglyceride, 1,2-diglyceride, 1,3-diglyceride, triglyceride, free fatty acid, phospholipid and pharmaceutically acceptable salts thereof. For example, they can also be used in combination with vegetable oil, fish oil, seal oil, microalgae oil, krill oil and crustacean oil (ex. shrimp oil). According to another example, they can also be used in combination with oil hydrolysate from vegetable oil, fish oil, seal oil, microalgae oil, krill oil and crustacean oil (ex. shrimp oil). According to another example they can be used in combination with proteins hydrolysate from vegetable, animal and marine source. Moreover, they can also be used to form micelle or liposome for a drug delivery system.

According to another example, the active agent can be a lipid or an hydrolysate thereof, or a protein or an hydrolysate thereof.

According to another example, the active agent can be chosen from a fatty acid, a salt thereof, an ester thereof (for example a monoglyceride, a diglyceride, or a triglyceride), and mixtures thereof.

According to another example, the active agent can be a fatty acid or a derivative thereof (for example an C1-C6 ester (C1-C6 being the amount of carbon atoms in the "alcohol"

portion of the ester) of a fatty acid such as an ethyl ester) or a pharmaceutically acceptable salt thereof.

According to another example, the active agent can be a polyunsaturated fatty acid chosen from arachidonic acid, ω3-arachidonic acid, alpha-linolenic acid, conjugated linoleic acid, linoleic acid, gamma-linolenic acid, dihomo-gamma-linolenic acid, stearidonic acid, eicosapentaenoic acid, ω3-docosapentaenoic acid, ω6-docosapentaenoic acid, docosahexaenoic acid, monoglycerides thereof, diglycerides thereof, triglycerides thereof, phospholipids thereof, and salts thereof.

According to another example, the active agent can be a compound chosen from compounds previously defined.

According to another example, the active agent can be chosen from any of the following therapeutic class: analgesic, anesthetic, anti-Alzheimer's, anti-asthma agent, anti-Parkinsonism, antiallergic, antianginal, antiarrhythmic, antiarthritic, antiasthmatic, antibacterial, antibiotic, anticancer, anticoagulant, antidepressant, antidiabetic, antiemetic, antiepileptic, antifungal, antiglaucoma, anti-gout, antihistamine, antihyperprolactinemia, antihypertensive, antiinflammatory, antimigraine, anti-neoplastic, antiobesity, antiparasitic, antiprotozoal, anti-phyretics, antipsoriatic, antipsychotic, antithrombotic, antiulcer, antiviral, anxiolytic, benign prostatic hypertrophy, bronchodilator, calcium metabolism, cardiotonic, cardiovascular agent, chelator & antidote, chemopreventive agent, contraception, diuretic, dopaminergic agent, gastrointestinal agent, gastroprokinetic, hematopoiesis, hemophilia, hormone, hormone replacement therapy, hypnotic, hypocholesterolemic, hypolipidemic, immunomodulator, immunostimulant, immunosuppressant, lipid regulating agent, male sexual dysfunction, multiple sclerosis, muscle relaxant, neuroleptic, nootropic, osteoporosis, phytoestrogen, platelet aggregation inhibitor, prostaglandin, radioenhencer for radiotherapy, relaxant and stimulant, respiratory distress syndrome, urinary incontinence, vasodilator, vitamin/nutritional, vulnerary and xanthine. Active agents belonging to these classes can be used in the previously mentioned compositions.

According to one example, the active agent can be a chemopreventive agent. The chemopreventive agent can be, for example, chosen from 13-cis-retinoic acid, 9-cis retinoic acid, anetholtrithione, arzoxifene hydrochloride, aspirin, bexarotene, biaxin (clarithromycin), budesonid, calcium, celecoxib, curcumin, DFMO, DHEA (Dehydroepiandrosterone), fenretinide, indole-3-carbinol, l-perillyl alcohol, lycopene, oltipraz, phenethyl isothiocyanate (PEITC), piroxicam, raloxifen, selenium, soy isoflavones, sulindac, tamoxifen, 4-hydroxy-tamoxifen, citrate, tea polyphenols, ursodiol, vitamin D and analogs, and zileuton.

According to another example, the active agent can be an antibacterial agent. Non-limitative examples of antibacterial agents are RV-11, carumonam, daptomycin, fosfomycin trometamol, isepamicin, micronomicin sulfate, miokamycin, mupirocin, netilimicin sulfate, teicoplanin, apalcillin sodium, arbekacin, aspoxicillin, astromycin sulfate, azithromycin, aztreonam, biapenem, cefbuperazone sodium, cefcapene pivoxil, cefdinir, cefditoren pivoxil, cefepime, cefetamet pivoxil HCl, cefixime, cefmenoxime HCl, cefminox, sodium, cefodizime sodium, cefonicid sodium, cefoperazone sodium, ceforanide, cefoselis, cefotetan disodium, cefotiam HCl, cefozopran HCl, cefpimizole, cefpiramide sodium, cefpirome sulfate, cefpodoxime proxetil, cefprozil, cefsoludin sodium, ceftazidime, cefteram pivoxil, ceftibuten, ceftizoxime sodium, ceftriaxone sodium, cefuroxime axetil, cefuzonam sodium, clarithromycin, dalfopristin, dirithromycin, doripenem, ertapenem sodium, erythromycin acistrate, flomoxef sodium, flurithromycin ethylsuccinate, fropenam, imipenem/cilastatin, lenampicillin HCl, loracarbef, meropenem, moxalactam disodium, panipenem/betamipron, quinupristin, rifabutin, rifamixin, rifapentine, rifaximin, rokitamycin, roxithromycin, sultamycillin tosylate, tazobactam sodium, telithromycin, temocillin disodium, tigecycline, balafloxacin, ciprofloxacin, enoxacin, fleroxacin, gatifloxacin, gemifloxacin mesilate, grepafloxacin, levofloxacin, linezolid, lomefloxacin, moxifloxacin HCl, nadifloxacin, norfloxacin, ofloxacin, pazufloxacin, pefloxacin mesylate, prulifloxacin, rufloxacin hydrochloride, sparfloxacin, taurolidine, temafloxacin hydrochloride, tosufloxacin, trovafloxacin mesylate, rodimoprin, ACWY meningoccal PS vaccine, MCV-4, h influenzae b vaccine, h influenzae b vaccine, meningitis b vaccine, meningococcal vaccine, oral cholera vaccine, pneumococcal vaccine, and vi polysaccharide typhoid vaccine According to another example, the active agent can be an antifungal agent. The antifungal agent can be, for example, chosen from interferon gamma-n1, anidulafungin, caspofungin acetate, micafungin sodium, amorolfine hydrochloride, butoconazole, ciclopirox, olamine, cloconazole HCl, eberconazole, fenticonazole nitrate, fluconazole, flutrimazole, fosfluconazole, itraconazole, ketoconazole, lanoconazole, luliconazole, naftifine HCl, neticonazole HCl, oxiconazole nitrate, posaconazole, sertaconazole nitrate, sulconazole nitrate, terconazole Gyno, tioconazole, voriconazole, butenafine hydrochloride, liranaftate, and terbinafine hydrochloride According to another example, the active agent can be an antiviral agent. Non-limiting examples of antiviral agents are: immunoglobulin intravenous, interferon alfa, interferon alfa-2b, interferon alfa-n3, interferon alfacon-1, interferon beta, palivizumab, peginterferon alfa-2a, peginterferon alfa-2b, resp syncytial virus IG, thymalfasin, interferon alfa-n1, enfuvirtide, zanamivir, delavirdine mesylate, efavirenz, foscarnet sodium, imiquimod, nevirapine, propagermanium, rimantadine HCl, oseltamivir, abacavir sulfate, acyclovir, adefovir dipivoxil, cidofovir, didanosine, emtricitabine, entecavir, epervudine, famciclovir, ganciclovir, inosine pranobex, lamivudine, penciclovir, sorivudine, stavudine, tenofovir disoproxil fumarate, valaciclovir HCl, valganciclovir, zalcitabine, zidovudine, amprenavir, atazanavir, darunavir, fomivirsen sodium, fosamprenevir, indinavir sulfate, lopinavir, nelfinavir mesylate, ritonavir, saquinavir mesylate, tipranavir, MR vaccine, anti-Hep B immunoglobulin, attenuated chicken pox vaccine, hepatitis A and B vaccine, hepatitis B vaccine, hepatitis a vaccine, inact hepatitis a, influenza vaccine, influenza virus (live), rotavirus vaccine, rubella vaccine, varicella virus vaccine, and zoster vaccine live.

According to another example, the active agent can be an antiparasitic agent. Non-limitative examples of antiparasitic agents are: Artemisinin, ivermectin, arteether, artemether, artenusate, eflornithine HCl, mefloquine HCl, albendazole, halofantrine, lumefantrine, quinfamide, atovaquone, bulaquine/chloroquine, and trichomonas vaccine According to another example, the active agent can be an anticancer agent. Non-limitative examples of anticancer agents are H-101, aldesleukin, alemtuzumab, bevacizumab, celmoleukin, cetuximab, denileukin, diftitox, interferon alfa2a, interferon alfa2b, interferon gamma-1a, interleukin-2, mobenakin, pegaspargase, rituximab, tasonermin, teceleukin, tositumomab, trastuzumab, aclarubicin, actinomycin D, angiotensin II, arglabin, asparaginase, bleomycin, carzinophilin, chromomycin A3, daunomycin, doxorubicin, leucovorin, masoprocol, mithramycin, mitomycin C, neocarzinostatin, paclitaxel, palictaxel nanoparticles, pentostatin, peplomycin, sarkomycin, solamargine (aka BEC), streptozocin pre-, taxotere, testosterone pre-, vinblastine, vincristine, alitretinoin, amrubicin HCl, belotecan hydrocholoride, calusterone, cladribine, cytarabine ocfosfate, dexamethasone, docetaxel, dromostanolone, elliptinium acetate, epirubicin HCl, estramustine, ethinyl estradiol pre-, toposide, exemestane, fluoxymesterone pre-, formestane, fosfestrol pre-, fulvestrant, gemtuzumab, ozogamicin, goserelin acetate, hexyl aminolevulinate, histrelin, hydroxyprogesterone pre-, idarubicin hydrochloride, irinotecan hydrochloride, leuprolide, medroxyprogesterone acetate, megesterol acetate, methylprednisolone, methyltestosterone, miltefosine, mitobronitol, nadrolone phenylpropionate, norethindrone acetate pre-, pirarubicin, prednisolone pre-, prednisone pre-, teniposide, testolactone, topotecan HCl, triamcinolone, triptorelin, valrubicin, vapreotide acetate vindesine, vinorelbine, zinostatin stimalamer, amsacrine, arsenic trioxide, bisantrene hydrochloride, busulfan, carboplatin, carmustine (BCNU), chlorambucil, chlortrianisene pre-, cis-diamminedichloroplatinum, cyclophosphamide, dacarbazine, diethylstilbestrol pre-, flutamide, fotemustine, heptaplatin/SK-2053R, hexamethylmelamine, hydroxyurea, ifosfamide, lenalidomide, levamisole pre-, lobaplatin, lomustine (CCNU), lonidamine, mechlorethanamine, melphalan, mitotane, nedaplatin, nilutamide, nimustine hydrochloride pre-, oxaliplatin, pamidronate, pipobroman, porfimer sodium, procarbazine, ranimustine, razoxane pre-, semustine (MCCNU) pre-, sobuzoxane, sorafenib mesylate, thiotepa, triethylenemelamine pre-, zoledronic acid, anastrozole, bicalutamide, bortezomib, camostat mesylate, dasatinib, erlotinib hydrochloride, fadrozole HCl, gefitinib, imatinib mesilate, letrozole, nafoxidine pre-, sunitinib maleate, tamoxifen, toremifene, aminoglutethimide, azacytidine pre-, apecitabine, carmofur, clofarabine, cytosine arabinoside, decitabine, doxifluridine, enocitabine, floxuridine, fludarabine phosphate, fluorouracil, ftorafur, gemcitabine HCl, mercaptopurine, methotrexate, mitoxantrone HCl, nelarabine, thioguanine, uracil mustard, abarelix, bexarotene, pemetrexed, raltitrexed, tamibarotene, temozolomide, bcg live, and melanoma theraccine According to another example, the active agent can be an antidiabetic agent. Non-limitative examples of antidiabetic agents are biphasic porcine insulin, hu neutral insulin, human insulin Zn suspension, human insulin zinc suspension, human neutral insulin, insulin aspart, insulin aspart/IA protamine, insulin detemir, insulin glargine, insulin glulisine, insulin lispro, isophane insulin, mecasermin, oral insulin, porcine isophane insulin, porcine neutral insulin, pulmonary insulin, soluble insulin, voglibose, acarbose, extenatide, miglitol, triproamylin acetate, glimepiride, mitiglinide calcium hydrate, pioglitazone, repaglinide, epalrestat, rosiglitazone maleate, toirestat, troglitazone, and nateglinide According to another example, the active agent can be a natural product or natural product crude extract chosen from a vegetable, mussels (for example, green lipped mussels), shrimps, fish, seal, microalgaee, krill, a crustacean; an hydrolysate from vegetable oil, fish oil, seal oil, microalgae oil, krill oil or crustacean oil, a vegetable oil, mussels oil (for example green lipped mussels oil), shrimps oil, fish oil, seal oil, microalgae oil, krill oil, a crustacean oil; and a proteins hydrolysate from vegetable, animal or marine source.

According to another example, the active agent can be an a natural product or natural product crude extract, which can be, for example, alfalfa, *aloe, angelica, arnica*, aristolochic acid, *artemisia*, astaxanthin, ashwaganda, *astragalus*, avens, beta-carotene, bilberry, birch, black cohosh, black horehound, blessed thistle, biotin, boldo, burdock, calcium, *calendula*, california poppy, caraway, cascara sagrada, catnip, cayenne, chaste tree fruit, chondroitin sulphate, copper, cramp bark, cranberry, dandelion, dang gui, devil's claw, *echinacea, echinacea purpurea, echinacea pallida*, eleuthero, evening primrose oil, european linden, european pennyroyal, fenugreek, feverfew, figwort, flax, folate, frankincense, garlic, gentian, ginger, *ginkgo*, globe artichoke, glucosamine, goldenseal, green tea, ground ivy, hawthorn, heal-all, hops, horse chestnut, horseradish, hyssop, *illicium verum*, juniper, licorice, linden, lungwort, lutein, melatonin, milk thistle, mugwort, niacin, pantothenic acid, peppermint, reishi mushroom, riboflavin, rosemary, saw palmetto, scullcap, selenium, *schisandra*, stinging nettle, St. John's wort, *thuja*, thyme, tomato, turmeric, valerian, willow bark, witch hazel or zeaxanthin.

According to another example, the active agent can be curcumin, artemisinin, astaxanthin, lutein, or zeaxanthin.

According to another example the active agent can be a turmeric crude extract or purified extract from turmeric crude extract, an *artemisia* crude extract or purified extract from *artemisia* crude extract, green lipped mussels crude extract or purified extract from green lipped mussels crude extract, a crude extract or purified extract of a microalgae.

According to another example the active agent can be a *Haematococcus pluvialis* microalgae crude extract or purified extract from *Haematococcus pluvialis* microalgae crude extract.

The person skilled in the art would be able to identify, among the active agents previously described, those that can be considered as lipophillic active agents.

According to another example, the at least one compound present in an oil can be a fatty acid or a derivative thereof (for example an C1-C6 ester (C1-C6 being the amount of carbon atoms in the "alcohol" portion of the ester) of a fatty acid such as an ethyl ester) or a pharmaceutically acceptable salt thereof.

According to another example, the oil can be a vegetable oil (such as flaxseed oil, pumpkinseed oil, canola oil, soybean oil, or walnut oil), fish oil (such as cod liver oil, salmon oil, tuna oil, shark oil, pelagic fishes oil, or sardine oil), seal oil, microalgae oil, krill oil, crustacean oil (for example shrimps oil), mussels oil (for example green lipped mussels oil), or mixtures thereof.

The sugar can be chosen from 5-carbon sugars and 6-carbon sugars. Non-limiting examples of 5-carbon sugar include ribose, arabinose, xylose, and lyxose. Non-limiting examples of 6-carbon sugar include glucose, galactose, mannose, allose, gulose, idose, talose, and altrose.

The sugar phosphate can be chosen from monosaccharides (such as mannose-6-phosphate, glucose-6-phosphate, galactose-6-phosphate, mannose-I-phosphate, glucose-I-phosphate and galactose-I-phosphate), disaccharides (such as 6-O-phosphoryl-a-D-mannopyranosyl-(1-2)-D-mannopyranose, 6-O-phosphoryl-a-D-mannopyranosyl-(1-3)-mannopyranose, 6-O-phosphoryl-a-D-mannopyranosyl-(1-6)-D-mannopyranose), trisaccharides (such as 6-O-phosphoryl-a-D-mannopyranosyl-(1-2)-D-mannopyranosyl-(1-2)-D-mannopyranose), and higher linear or branched oligosaccharides (such as pentamannose-6-phosphate).

The amino acid can be chosen from alanine, arginine, asparagine, aspartic acid, cysteine, glutamine, glutamic acid, glycine, isoleucine, leucine, lysine, methionine, phenylalanine, proline, serine, threonine, tryptophan, tyrosine, and valine.

The peptide can be chosen from any possible combination of the amino acids previously described.

The compounds and compositions previously defined can be in a mixture with a vegetable oil (such as flaxseed oil, pumpkinseed oil, canola oil, soybean oil, or walnut oil) a marine oil (such as algae oil, seal oil, krill oil, crustacean oil, or fish oil (for example cod liver oil, salmon oil, tuna oil, shark oil, pelagic fishes oil, or sardine oil), or an hydrolysate.

The term "aryl" as used herein refers to a cyclic or polycyclic aromatic ring. For example, the aryl group can be phenyl or napthyl.

The expression "aromatic heterocycle" as used herein refers to an aromatic cyclic or fused polycyclic ring system having at least one heteroatom selected from the group consisting of N, O, S and P. Non-limitative examples include heteroaryl groups are furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The expression "non-aromatic heterocycle" includes non-aromatic rings or ring systems that contain at least one ring having at least one hetero atom (such as nitrogen, oxygen, sulfur or phosphorus). This term includes, in a non-limitative manner all of the fully saturated and partially unsaturated derivatives of the above mentioned aromatic heterocycles groups. Examples of non-aromatic heterocycle groups include, in a non-limitative manner, pyrrolidinyl, tetrahydrofuranyl, morpholinyl, thiomorpholinyl, piperidinyl, piperazinyl, thiazolidinyl, isothiazolidinyl, and imidazolidinyl.

The term "crude extract" refers to an unpurified extract. Such an extract can be obtained, for example, by means of a supercritical fluid extract (for example carbon dioxide or an alkane), by using a solvent as ethanol, methanol, isopropanol, acetone or water, or by hydrodistillation.

The expression "lipophilic active agent" as used herein refers to an active agent which has an affinity for, or capability of dissolving in, lipids; i.e., non-water soluble oils, fats, sterols, triglycerides and the like.

The term "lipid" as used herein refers to as any fat-soluble (lipophilic), molecules, such as fats, fat-like substances, oils (such as animal oil, marine oil or vegetable oil), waxes, sterols (such as cholesterol, ergosterol, sitosterol, stigmasterol, fat-soluble vitamins (such as vitamins A, D, E and K), fatty acids, esters thereof, and various derivatives thereof such as monoglycerides, diglycerides, triglycerides, phospholipids, glycolipids, and cerebrosides.

The term "fatty acid(s)" as used herein refers to long chain aliphatic acids (alkanoic acids) of varying chain lengths, from about C12 to C22 (although both longer and shorter chain-length acids are known). For example, the predominant chain lengths are about C16 to about C22. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the 9th and 10th carbon atom as for palmitoleic acid (16:1) and oleic acid (18:1)), while "polyunsaturated fatty acids" (or "PUFAs") have at least two double bonds along the carbon backbone (e.g., between the 9th and 10th, and 12th and 13th carbon atoms for linoleic acid (18:2); and between the 9th and 10th, 12th and 13th, and 15th and 16th for [alpha]-linolenic acid (18:3)).

"PUFAs" can be classified into two major families (depending on the position (n) of the first double bond nearest the methyl end of the fatty acid carbon chain). Thus, the "[omega]-6 fatty acids" [omega]-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "[omega]-3 fatty acids" ([omega]-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

The expression "inflammatory disease(s)" as used herein refers to all of the acute or chronic inflammatory diseases associated with the excessive release of cytokines, and complication thereof. The expression "chronic inflammatory disease(s)" refers to all diseases that induce tissue injury or induce continuous inflammation due to hyperactivity and the excessive release of cytokines, and complication thereof. In particular, the inflammatory diseases to which the compounds and compositions of the present disclosure can be applied are not limited to, but include inflammatory bowel disease such as Crohn's disease and ulcerative colitis, peritonitis, osteomyelitis, cellulitis, meningitis, cerebritis, pancreatitis, trauma-inducing shock, bronchial asthma, allergic rhinitis, cystic fibrosis, cerebral apoplexy, acute bronchitis, chronic bronchitis, acute bronchiolitis, chronic bronchiolitis, osteoarthritis, gout, spinal arthropathy, ankylosing spondylitis, Reiter's syndrome, psoriatic arthropathy, enteropathic spondylitis, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with 'vasculitis syndrome', polyarteritis nodosa, hypersensitivity vasculitis, Wegener's granulomatosis, polymyalgia rheumatica, giant cell arteritis, calcium crystal deposition arthropathy, pseudogout, nonjoint rheumatism, bursitis, tenosynovitis, epicondylitis (tennis elbow), neuropathic joint disease (charcot joint), hemarthrosic, Henoch-Schonlein purpura, hypertrophic osteoarthropathy, multicentric reticulohistiocytoma, scoliosis, hemochromoatosis, meniscocytosis, other hemoglobinopathy, hyperlipoproteinemia, hypogammaglobulinaemia, familial Mediterranean fever, Gerhardt Disease, systemic lupus erythematosus, relapsing fever, psoriasis, multiple sclerosis, sepsis (septicemia), septic shock, acute respiratory distress syndrome, multiple organ dysfunction syndrome, chronic obstructive pulmonary disease, rheumatic arthritis, acute lung injury, bronchopulmonary dysplasia and so on.

The expression "effective amount" of a compound of the present disclosure or of a composition of the present disclosure is a quantity sufficient to, when administered to the subject, including a mammal, for example a human, effect beneficial or desired results, including clinical results, and, as such, an "effective amount" or synonym thereto depends upon the context in which it is being applied. For example, in the context of treating cancer, for example, it is an amount of the compound sufficient to achieve such treatment of the cancer as compared to the response obtained without administration of the compound. The amount of a given compound of the present disclosure that will correspond to an effective amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, an "effective amount" of a compound of the present disclosure is an amount which inhibits, suppresses or reduces a cancer (e.g., as determined by clinical symptoms or the amount of cancerous cells) in a subject as compared to a control. The same definition of "effective amount" also applies when the compounds of the present disclosure are used for inhibiting tumor growth, inhibiting tumor cell proliferation, reducing tumor growth, or enhancing bioavailability of an active agent, or treating an inflammatory disease.

The term "subject" as used herein includes all members of the animal kingdom including human. According to one embodiment, the subject is a human.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt. In embodiments of the present disclosure, the pharmaceutically acceptable acid addition salt is the hydrochloride salt.

The term "pharmaceutically acceptable basic addition salt" as used herein means any non-toxic organic or inorganic base addition salt of any acid compound of the disclosure, or any of its intermediates. Acidic compounds of the disclosure that may form a basic addition salt include, for example, where R is $CO_2H$. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

Compounds of the present disclosure include radiolabeled forms, for example, compounds labeled by incorporation within the structure $^2H$, $^3H$, $^{14}C$, $^{15}N$, or a radioactive halogen such as $^{125}I$. A radiolabeled compound of the compounds of the present disclosure may be prepared using standard methods known in the art.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The compounds and compositions described in the present disclosure can be useful for chemoprevention of cancer, treating cancer, inhibiting tumor growth, reducing tumor growth the prevention or treatment of cardiovascular disease, the prevention or treatment of neurodegenerative diseases, the prevention or treatment of inflammation or of an inflammatory disease, the prevention or treatment of age-related eye disease.

The compounds and compositions described in the present disclosure can also be useful for in a self-emulsifying drug delivery systems (SEDDS), a self-microemulsifying drug delivery systems (SMEDDS) or a selfemulsifying oil formulations (SEOF). They can also be used for oral delivery of lipophilic drugs, natural product or natural crude extract, as an oral bioavailability enhancer of docosahexaenoic acid, ω3-docosapentaenoic acid, ω6-docosapentaenoic acid or eicosapentaenoic acid, or for preparing a micelle or liposome for a drug delivery system.

For example, the compounds previously defined can be of formulas:

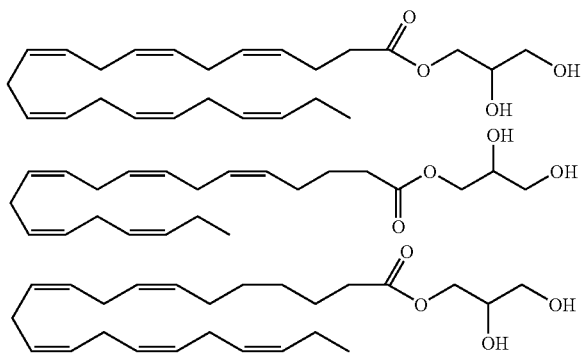

| 17 | 18 |
|---|---|
| -continued | -continued |
| 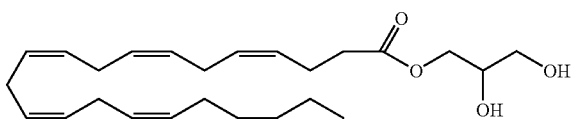 | 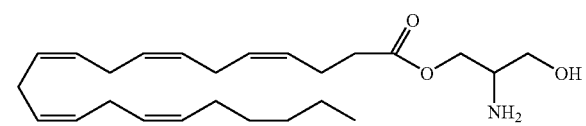 |
| 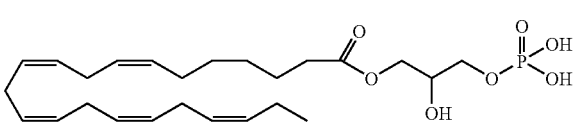 | 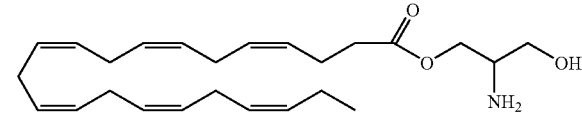 |
| 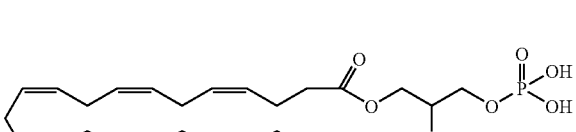 | 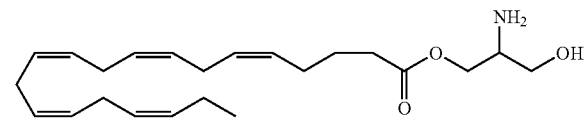 |
| 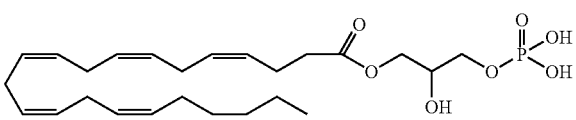 | 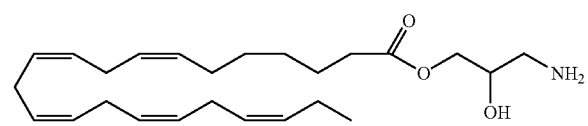 |
| 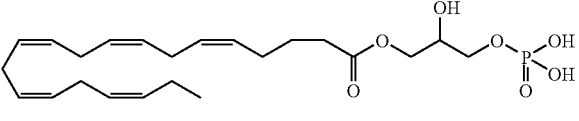 | 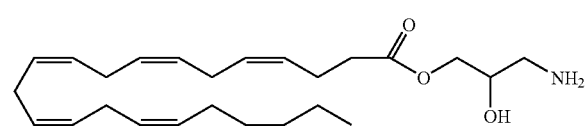 |
| 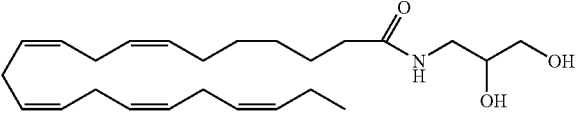 | 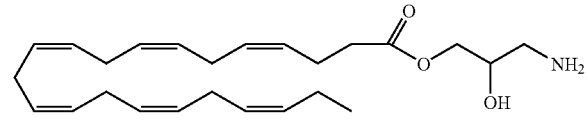 |
| 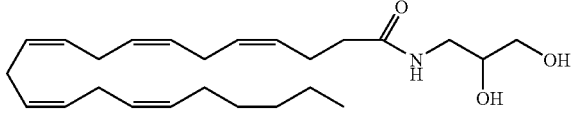 | 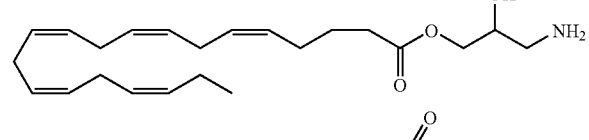 |
| 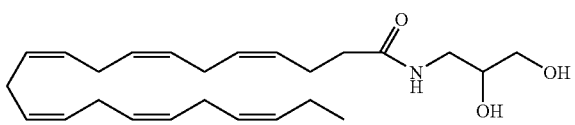 | 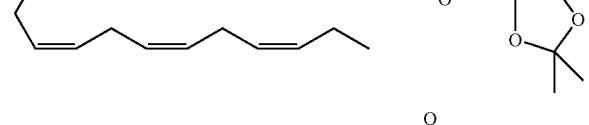 |
| 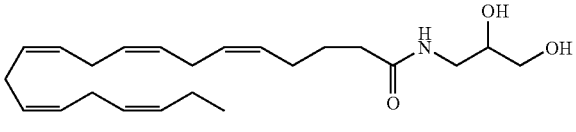 | 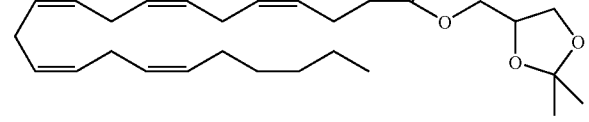 |
| 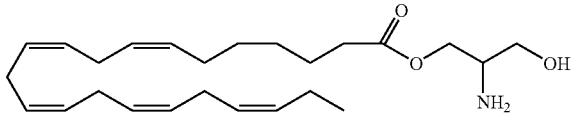 | 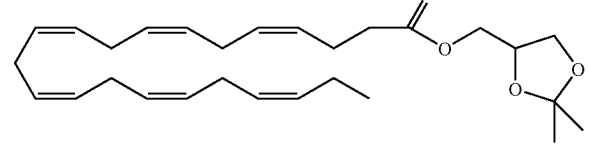 |
| | 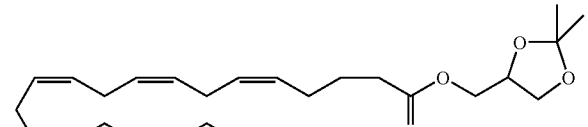 |

19
-continued
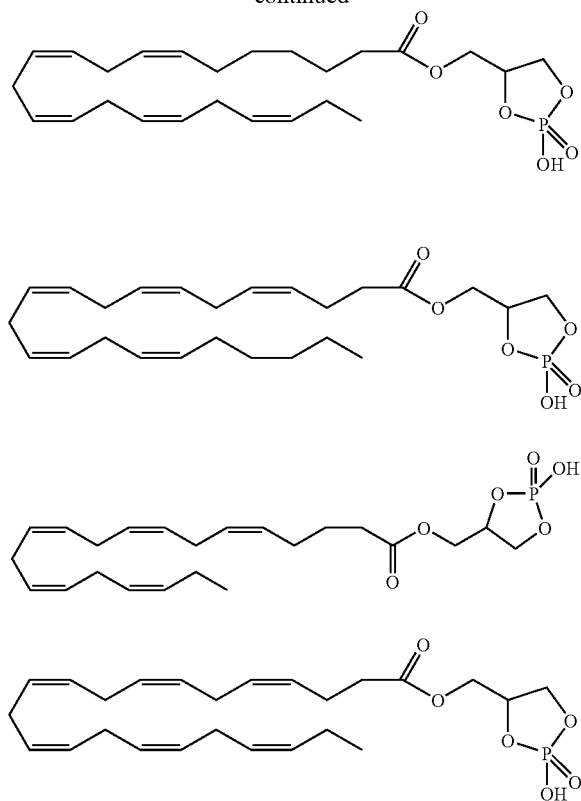
20
-continued
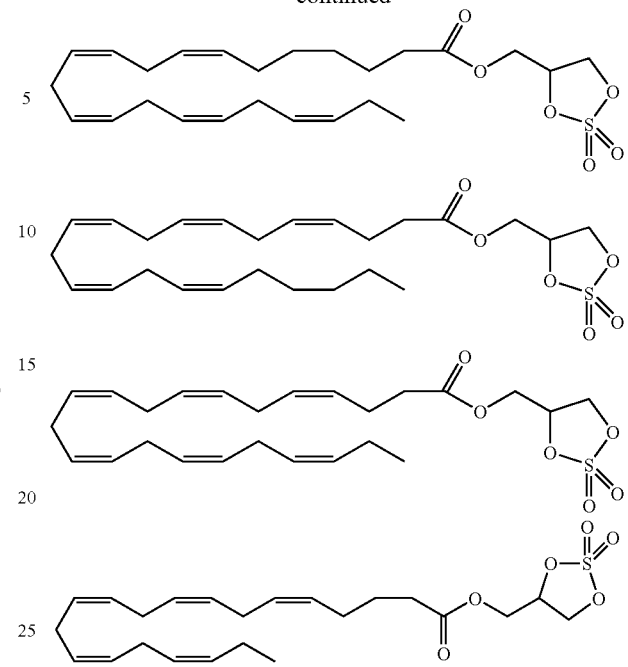
EXAMPLE 1
Preparation of Monoglyceride 1
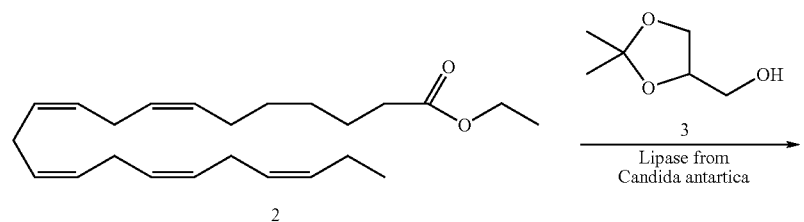
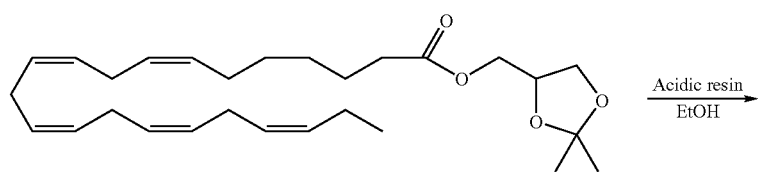
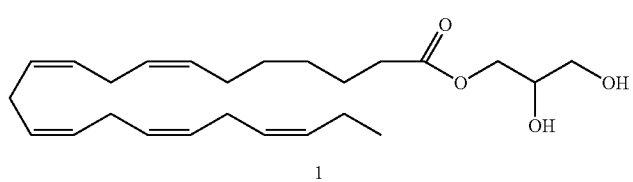

Docosapentaenoic acid ethyl ester (compound 2) (10 g) and compound 3 (6 g) were mixed together and heated at a temperature of 60° C. The enzyme (100 mg) was added and the reaction mixture was stirred at 60° C. under vacuum (18 mbar) or under nitrogen bubbling for 5 h. The reaction mixture was filtered and the enzyme was washed with ethanol 95% (20 ml). The acidic resin (500 mg) or organic acid was added to the ethanol solution and heated to reflux for 18 h. The resin was removed by filtration and the ethanol was evaporated in vacuo. The resulting crude product was dissolved in a mixture of hexanes/ethyl acetate 90:10 (10 ml) and silica gel (40 g) was added. The slurry was put on a fritted funnel and eluted with hexanes/ethyl acetate 90:10 (150 ml) to remove unreacted starting material. A second elution with ethyl acetate (300 ml) give, after evaporation in vacuo, the pure compound 1 (8.7 g) was tested in vitro on the cell viability assay and in an in vivo xenograft tumor model.

Pure compounds 5 and 6 (see below) have also been successfully prepared by following the same procedure.

EXAMPLE 2

Preparation of a Composition (Composition 1) Comprising Various Monoglycerides (Compounds 1, 5 and 6)

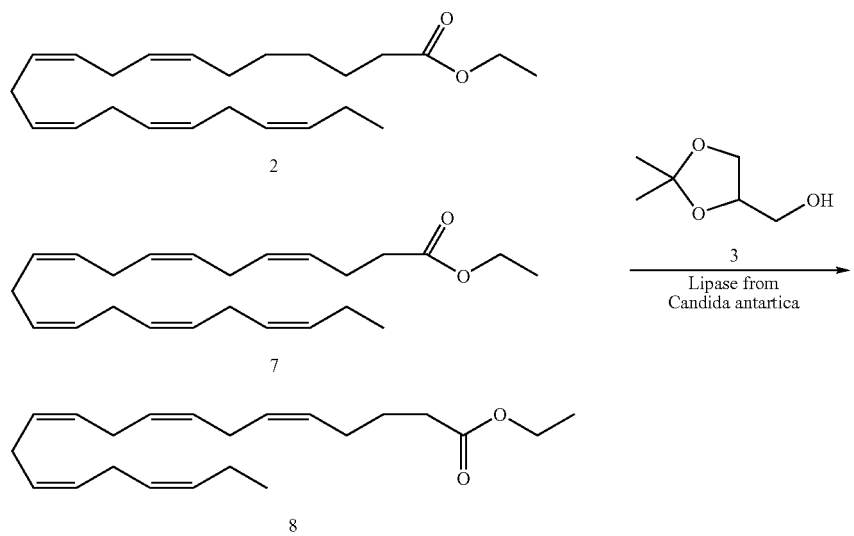

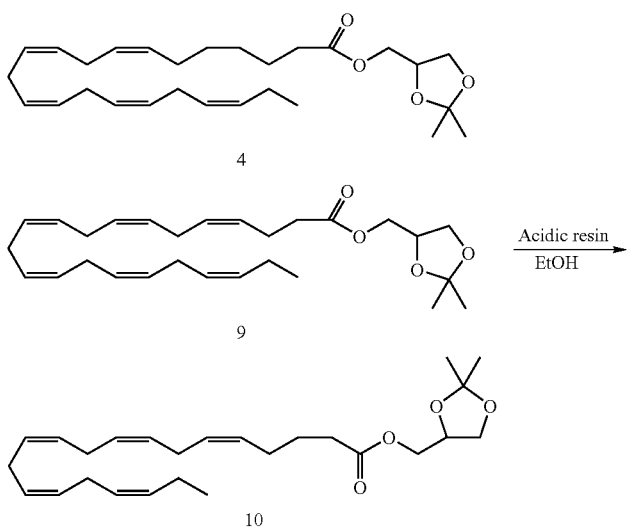

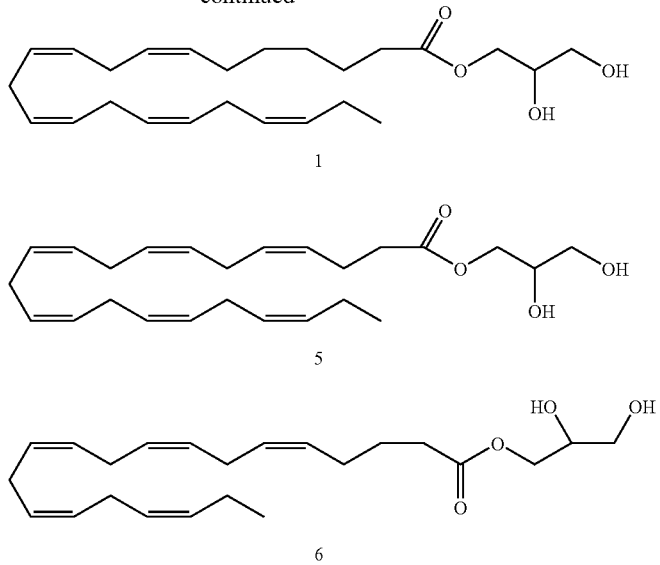

Composition 1 comprising compounds 1, 5 and 6 was prepared according to the same procedure as previously described in Example 1. The starting material was a mixture of compounds 2, 7, and 8 at respectively (10%, 80%, and 10%). This starting material composition was sold by the Company CRODA™ Chemical Europe Ltd. under the name INCROMEGA™ DHA 700 E SR. Thus, the obtained composition 1 contains 10% of compound 1, 80% of compound 5, and 10% of compound 6.

EXAMPLE 3

Freshly purified curcumin (10 mg) was dissolved in DMSO (1 ml). Five consecutive dilutions with a equal volume of DMSO was performed. PBS was added to the six stock solutions to a final volume of 1% DMSO for the in vitro assay. Precipitation occur at high concentration of curcumin. To solve the problem, curcumin (5 mg) was dissolve in a composition 1 (5 mg) and DMSO (1 ml) was added. Five consecutive dilutions with a equal volume of DMSO was performed. PBS was added to the six stock solutions to a final volume of 1% DMSO for the in vitro assay.

The cell viability assay is performed to measure the relative cell viability status of cancer cells upon exposure to test compounds in comparison to a positive control (etoposide) and a negative control (vehicule). Adherent cells growing in 96-well plates are exposed to test compounds for 3 days (72 hours). Four cancer cell lines including lung, colon, prostate and breast types are used since these types of cancer possess high incidence in human. Test compounds (composition 1 comprising compounds 1, 5 and 6) as well as positive and negative controls were tested in parallel on the same culture plate. All conditions are tested in triplicate. Apoptotic agents such as etoposide or epigallo-catechin-gallate are used as positive controls to kill cells whereas the solvent (dimethyl-sulfoxide and water) is used as negative controls for basal determination. Inhibition of 50% of cell growth compared to basal condition is the lower limit indicating a positive biological response (considered as a hit). After the incubation time, total protein content is quantified following staining with the anionic dye sulforhodamine B (SRB). The detection of luminescence, emitted by SRB, is completed by a microplate reader. This method of detection is based upon works published by Monks et al., in Journal of the National Cancer Institute vol. 82 no. 13 (1991) p. 757, Skehan et al. in Journal of the National Cancer Institute vol. 82 no. 13 (1990) p. 1107 and Rubinstein et al. in Journal of the National Cancer Institute vol. 82 no. 13 (1990) p. 1113. The amount of luminescence is directly proportional to the number of living cells in culture.

Cancer cells were grown in T-75 flask (Falcon) containing 20 ml of appropriate culture medium, subcultured twice a week at 37° C., 5% $CO_2$, 95% air and 100% relative humidity and maintained at low passage number (5 to 20), following manufacturer recommendations. The cell lines used were A-549 (human lung carcinoma), HCT-15 (human colon adenocarcinoma), BT-549 (human breast ductal carcinoma) and PC3 (human prostate adenocarcinoma). Cells were trypsinized using 0.25% trypsine (w/v)/0.53 mM EDTA solution (Hyclone), counted and plated at densities between 1000 and 3000 cells per well in flat bottom 96-well clear plates (Becton Dickinson) in 100 μl of appropriate culture medium supplemented with fetal bovine serum (Hyclone). Culture plates were incubated at 37° C., 5% $CO_2$, 95% air and 100% relative humidity for 72 hours. At 20-30% of cell confluence, 80 μl of appropriate culture medium was added to each well. 20 μl of either a solution of test compounds in 6 differents concentration, drug for positive controls (at concentration of 29 mg/ml) or solvent (vehicle or water) for negative controls were added on top of the 180 μl of culture medium to obtain a final volume of 200 μl. Background plate containing the same volume of medium without cells were included in each experiment. Microplates containing cells and test compounds were incubated at 37° C., 5% $CO_2$, 95% air and 100% relative humidity for 72 hours. One microplate for each cell line were fixed as described below. These four microplates represented basal growth at time zero. After incubation time of 72 hours, cells were fixed with 50 μl of cold (4° C.) 50% (w/v) trichloroacetic acid (TCA) added to the top of 200 μl of culture medium. These microplates contained conditions of growth control and test growth. Microplates were left 60 minutes at 4° C. and subsequently wash five times with 200 μl of deionized water. Microplates were left to dry at room temperature for at least 24 hours. All microplates were fixed with 100 μl of cold 0.4% (w/v) SRB dissolved in 1% acetic acid solution in water added to each well containing cells and left at room temperature for 10 minutes. Unbound SRB was removed with successive washes (five times) with 200 µl of cold 1% acetic acid solution in water. All microplates were left to dry at room temperature for at least 24 hours. Bound SRB to proteins was solubilised with the addition of 100 µl of 10 mM cold unbuffered Tris-base solution (pH 10.5). Microplates were left on a plate shaker for 5 minutes. Absorbance was read at 515 nm using a 96-well plate Multiskan Spectrum luminescence reader (Thermo Electron Corporation). Data analysis was performed using Excel 2003 and SigmaPlot 8.0 or GraphPad-Prism 3.02 software. Percent growth inhibition was calculated using the absorbance measurements [Growth at time zero ($T_0$), growth control (C) plus the test growth at the drug concentrations tested ($T_i$) as follows: $(T_i-T_0)/(C-T_0)\times 100$]. The results obtained are shown in FIGS. 1 to 9.

FIG. 1 represents the in vitro cell viability assay of six different concentrations of composition 1 on A-549 human lung cancer cell line. The positive control etoposide at 294 µg/ml shows 100% growth inhibition. The 50% growth inhibition is around 25 µg/ml of the tested composition.

FIG. 2 represents the in vitro cell viability assay of six different concentrations of purified curcumin on A-549 human lung cancer cell line. The positive control etoposide at 294 µg/ml shows 100% growth inhibition. The 50% growth inhibition is around 100 µg/ml of curcumin FIG. 3 represents the in vitro cell viability assay of six different concentrations of purified curcumin formulated with composition 1 on A-549 human lung cancer cell line. The positive control etoposide at 294 µg/ml shows 100% growth inhibition. The 50% growth inhibition is around 6.25 µg/ml of the tested composition.

Purified curcumin formulated in composition 1 decreases significantly the concentration needed to reach the 50% growth inhibition of A-549 human lung cancer cell line (see FIG. 3) as compared to purified curcumin (see FIG. 2) or composition 1 alone (see FIG. 1). The 50% growth inhibition concentration of purified curcumin alone is around 100 µg/ml and the 50% growth inhibition concentration of same purified curcumin formulated in composition 1 is around 3.13 µg/ml, a more than 30 times improvement of potency.

Figure 4:
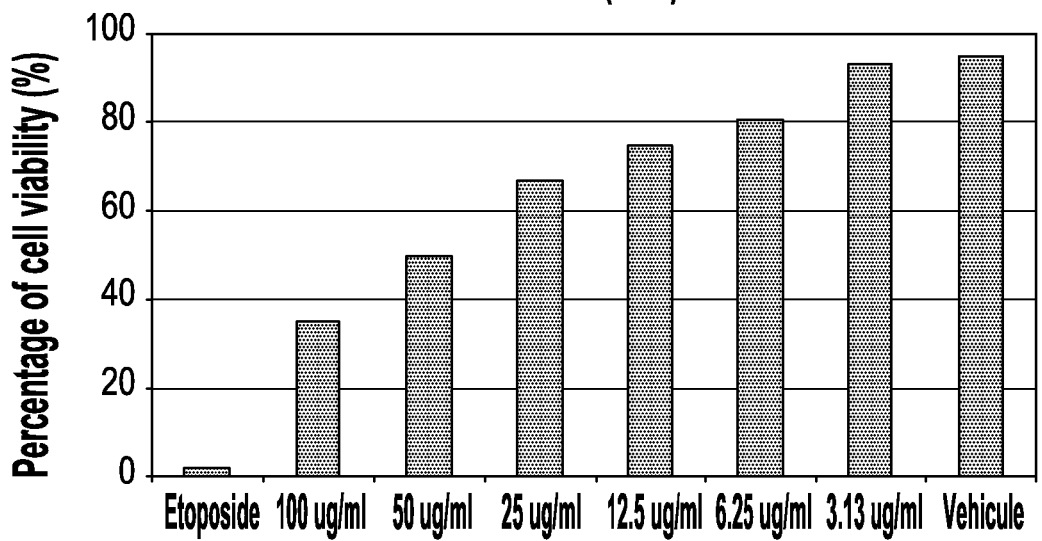
FIG. 4 represents an in vitro assay of a composition according to another example, wherein the assay was carried out on PC3 human cancer cell line.

FIG. 4 represents the in vitro cell viability assay of six different concentrations of composition 1 on PC-3 human prostate cancer cell line. The positive control etoposide at 294 µg/ml shows 100% growth inhibition. The 50% growth inhibition is around 50 µg/ml of the tested composition.

Figure 5:
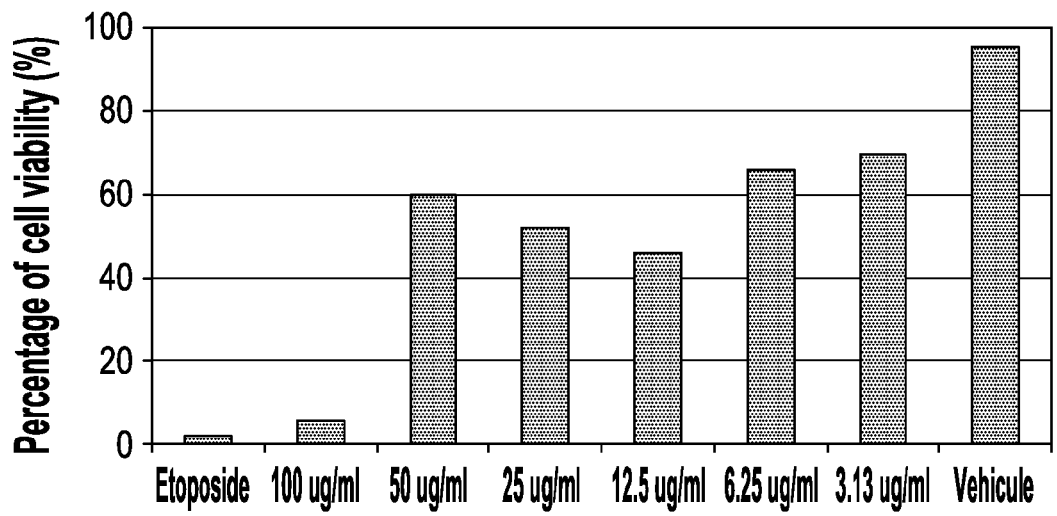
FIG. 5 represents an in vitro assay of a composition according to another example, wherein the assay was carried out on PC3 human cancer cell line.

FIG. 5 represents the in vitro cell viability assay of six different concentrations of purified curcumin on PC-3 human prostate cancer cell line. The positive control etoposide at 294 µg/ml shows 100% growth inhibition. The 50% growth inhibition is around 75 µg/ml of curcumin.

Figure 6:
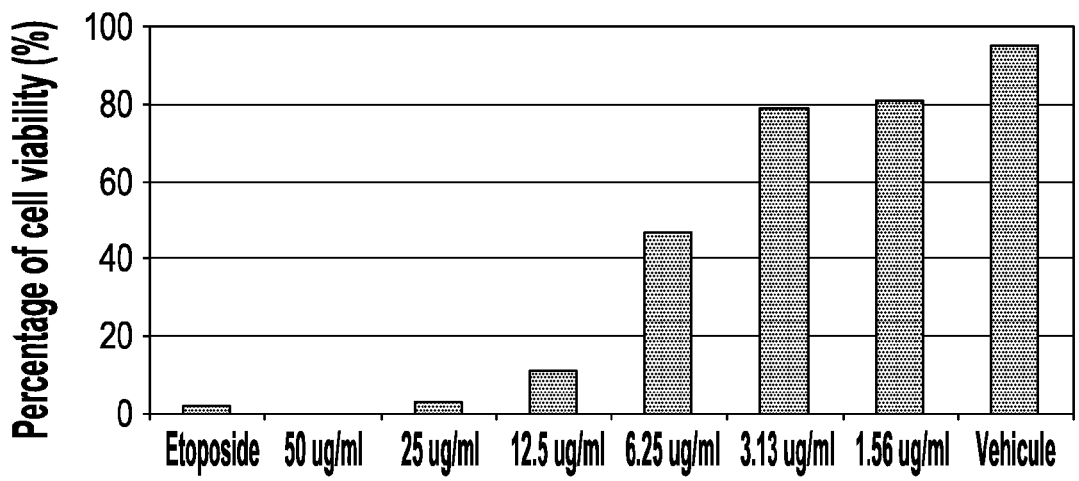
FIG. 6 represents an in vitro assay of a composition according to another example, wherein the assay was carried out on PC3 human cancer cell line.

FIG. 6 represents the in vitro cell viability assay of six different concentrations of purified curcumin formulated with composition 1 on PC-3 human prostate cancer cell line. The positive control etoposide at 294 µg/ml shows 100% growth inhibition. The 50% growth inhibition is around 6.25 µg/ml of the tested composition.

Purified curcumin formulated in composition 1 decreases significantly the concentration needed to reach the 50% growth inhibition of PC-3 human prostate cancer cell line (see FIG. 6) as compared to purified curcumin (see FIG. 5) or composition 1 alone (see FIG. 4). The 50% growth inhibition concentration of purified curcumin alone is around 75 µg/ml and the 50% growth inhibition concentration of same purified curcumin formulated in composition 1 is around 3.13 µg/ml, a more than 20 times improvement of potency.

Figure 7:
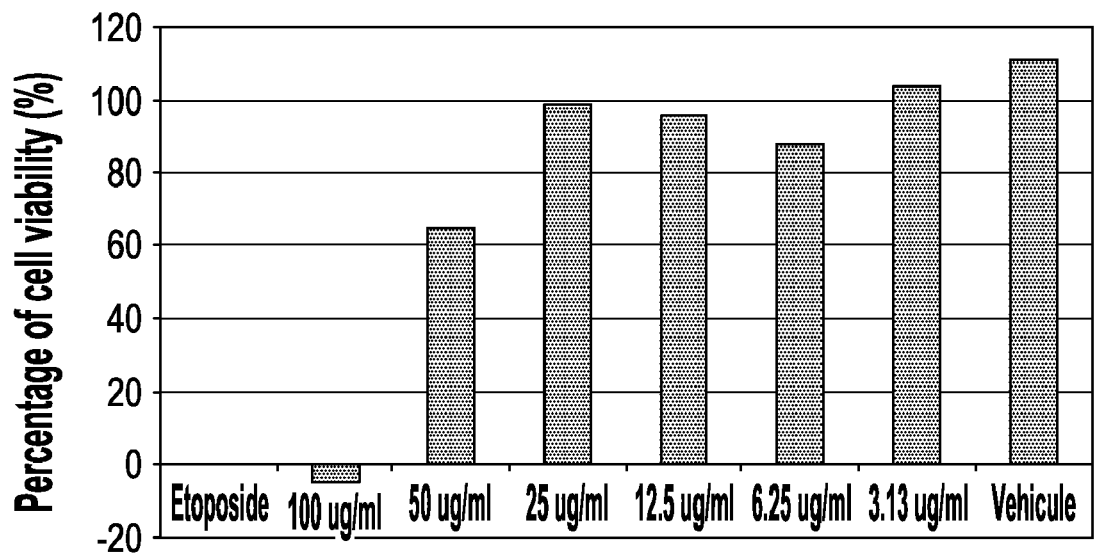
FIG. 7 represents an in vitro assay of a composition according to another example, wherein the assay was carried out on HCT-15 human cancer cell line.

FIG. 7 represents the in vitro cell viability assay of six different concentrations of composition 1 on HCT-15 human colon cancer cell line. The positive control etoposide at 294 µg/ml shows 100% growth inhibition. The 50% growth inhibition is around 75 µg/ml of the tested composition.

Figure 8:
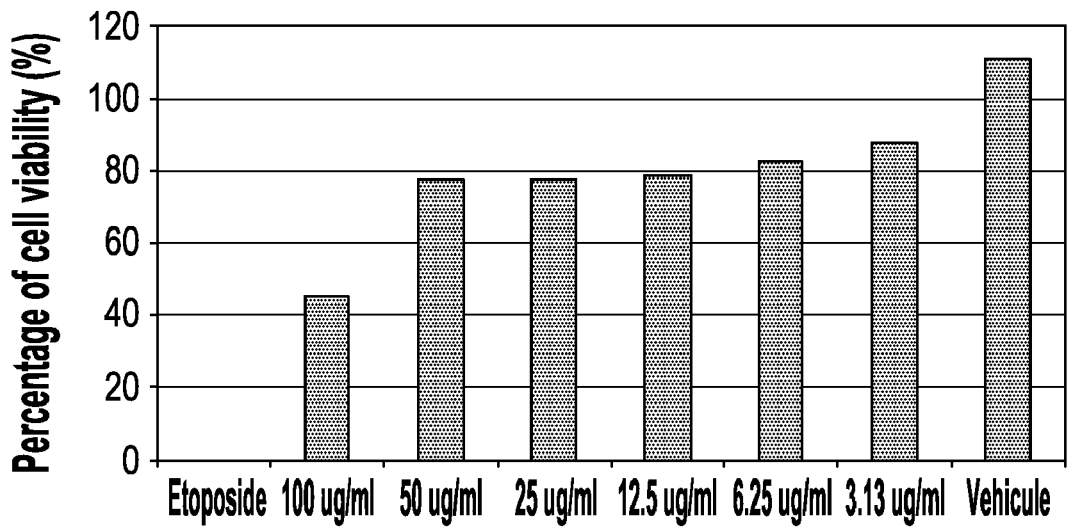
FIG. 8 represents an in vitro assay of a composition according to another example, wherein the assay was carried out on HCT-15 human cancer cell line.

FIG. 8 represents the in vitro cell viability assay of six different concentrations of purified curcumin on HCT-15 human colon cancer cell line. The positive control etoposide at 294 µg/ml shows 100% growth inhibition. The 50% growth inhibition is around 100 µg/ml of curcumin.

Figure 9:
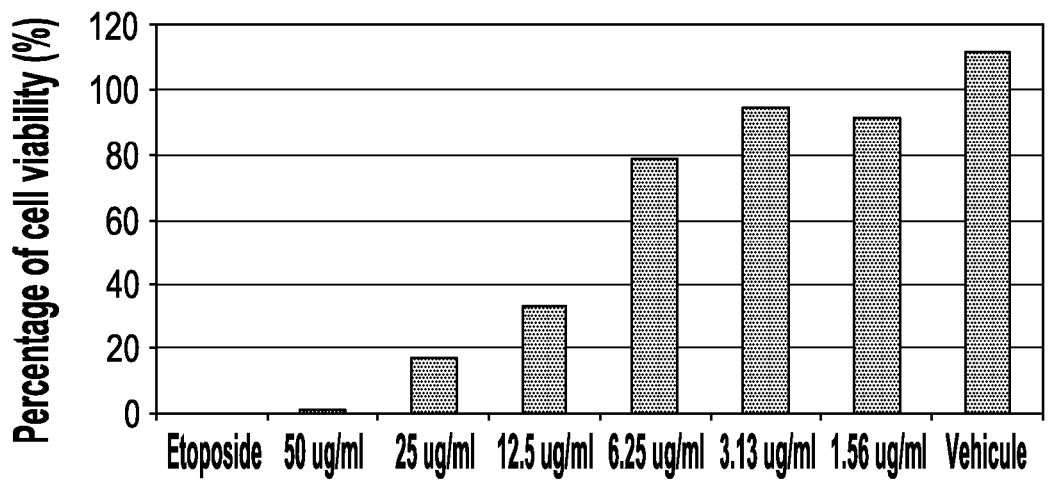
FIG. 9 represents an in vitro assay of a composition according to another example, wherein the assay was carried out on HCT-15 human cancer cell line.

FIG. 9 represents the in vitro cell viability assay of six different concentrations of purified curcumin formulated with composition 1 on HCT-15 human colon cancer cell line. The positive control etoposide at 294 µg/ml shows 100% growth inhibition. The 50% growth inhibition is around 12.5 µg/ml of the tested composition.

Purified curcumin formulated in composition 1 decreases significantly the concentration needed to reach the 50% growth inhibition of HCT-15 human colon cancer cell line (see FIG. 9) as compared to purified curcumin (see FIG. 8) or composition 1 alone (see FIG. 7). The 50% growth inhibition concentration of purified curcumin alone is around 100 µg/ml and the 50% growth inhibition concentration of same purified curcumin formulated in composition 1 is around 6.25 µg/ml, a more than 15 times improvement of potency.

EXAMPLE 4

In order to determine the solubility of various compounds in a fish oil as compared to their solubility in composition 1, a first sample of turmeric oleoresin (100 mg) obtained from ethanol extraction was stirred at room temperature in a fish oil (1.0 g) for 30 minutes. Then, another sample of turmeric oleoresin (100 mg) (also obtained from ethanol extraction) was stirred at room temperature in composition 1 (1.0 g) for 30 minutes. Both resulting suspensions were centrifuged at 12000 RPM for 5 minutes and 10 µl of each supernatant was dissolved in DMSO and further dilution was made to meet the linearity range of HPLC/MS method for the quantification of curcuminoids (0.001 µg/ml to 0.1 µg/ml). The comparative results obtained concerning the solubility of some components of the turmeric oleoresin extract (bis-demethoxycurcumin, demetoxycurcumin, curcumin and total curcuminoids) in the fish oil and in the composition 1 are shown in FIG. 10.

Figure 10:
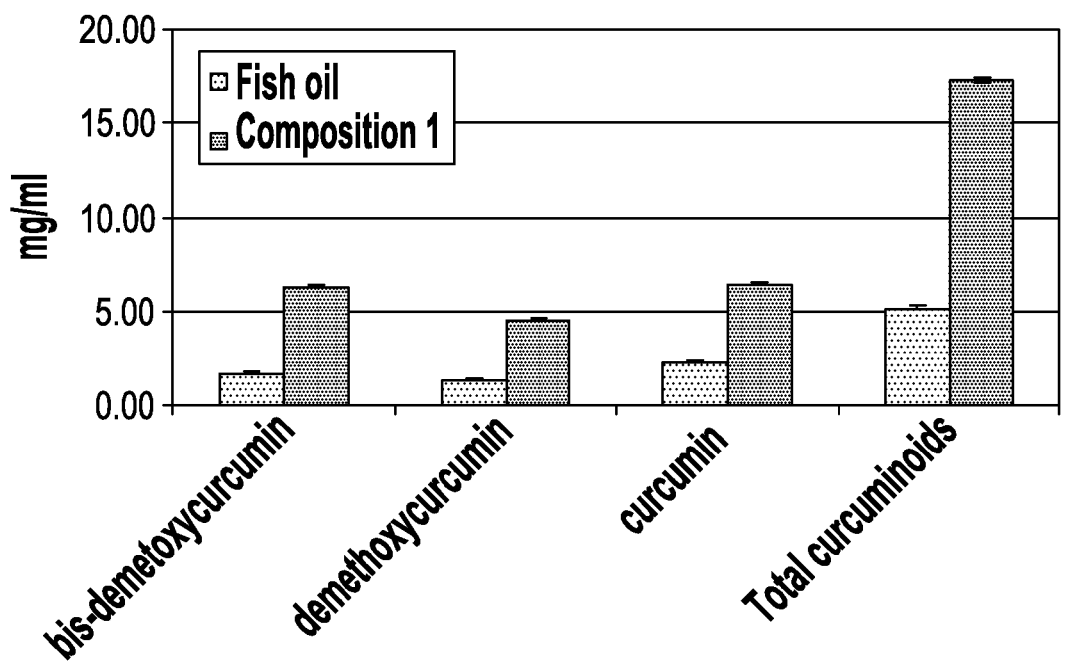
FIG. 10 represents a comparative solubility study of bis-demethoxycurcumin, demetoxycurcumin, curcumin and total curcuminoids in two different solvents which are a fish oil and a composition according to another example.

As it can be seen in FIG. 10, composition 1 permits to enhance the solubility of various active agents (bis-demethoxycurcumin, demetoxycurcumin, curcumin and total curcuminoids) in a lipid or lipid formulation. It can be clearly seen from FIG. 10 that such active agents have a greater solubility in a lipid formulation consisting of composition 1 than in a lipid formulation consisting of a fish oil. As it can be seen, the active agents are about 3 to 4 times more soluble in composition 1 than in a fish oil. It can thus also be seen the that such a composition is effective for solubilizing lipophilic active agents.

EXAMPLE 5

The relative in vivo bioavailability of two different formulations containing docosahexaenoic acid which are a fish oil and composition 1 was determined by a pharmacokinetic study. Upon arrival in the animal facility, the male Sprague-Dawley rats were marked for identification and weighed. The animals were acclimatized for 1 week before commencing the study. On the day of the study, shortly before dosing, the animals were re-weighed and placed into experimental groups based on a distribution of weight. Animals received food and water ad libitum except during the pharmacokinetic study (from overnight to Bleed Time 480 minutes). The animals were not deprived of food overnight from Bleed Time 480 to 1440 minutes since the length of the pharmacokinetic study was 24 hours. The compound dosing solutions were administered orally as a single slow bolus (over approximately 15 seconds) according to standard procedures for administration of solution by gavage: the animal was firmly restrained; a bulb-tipped gastric gavage needle of 18G was passed through the side of the mouth and was moved forward toward the oesophagus. The dosing solutions were dosed orally at 3 g/kg by adjusting the dose volume (3 mL/kg) according to the body weight of each animal and the density of the compound ~1 g/mL). Blood samples were collected prior to compound administration and at different time points following administration. Blood samples (200 µl) from each animal were collected by veinipuncture, under isoflurane anaesthesia according to the following standard operating procedure for blood collection via the jugular vein: animals were placed in a supine position on a slanted board to allow the head to be lower than the lower extremities. The upper extremities were extended at a 90° angle and the neck extended and turned gently towards the site of blood collection. A 22-gauge 1" needle was inserted underneath the clavicle while aspirating.

For plasma preparation, blood samples were placed into tubes containing EDTA, mixed gently to assure anticoagulation and put on ice. Plasma separation was performed following centrifugation of the blood samples. Plasma was transferred into a tube and stored at −80° C. pending shipment for analysis. The pellet was kept in the initial tube containing EDTA and stored at −80° C. pending shipment. The results of this study are shown in FIG. 11.

Figure 11:
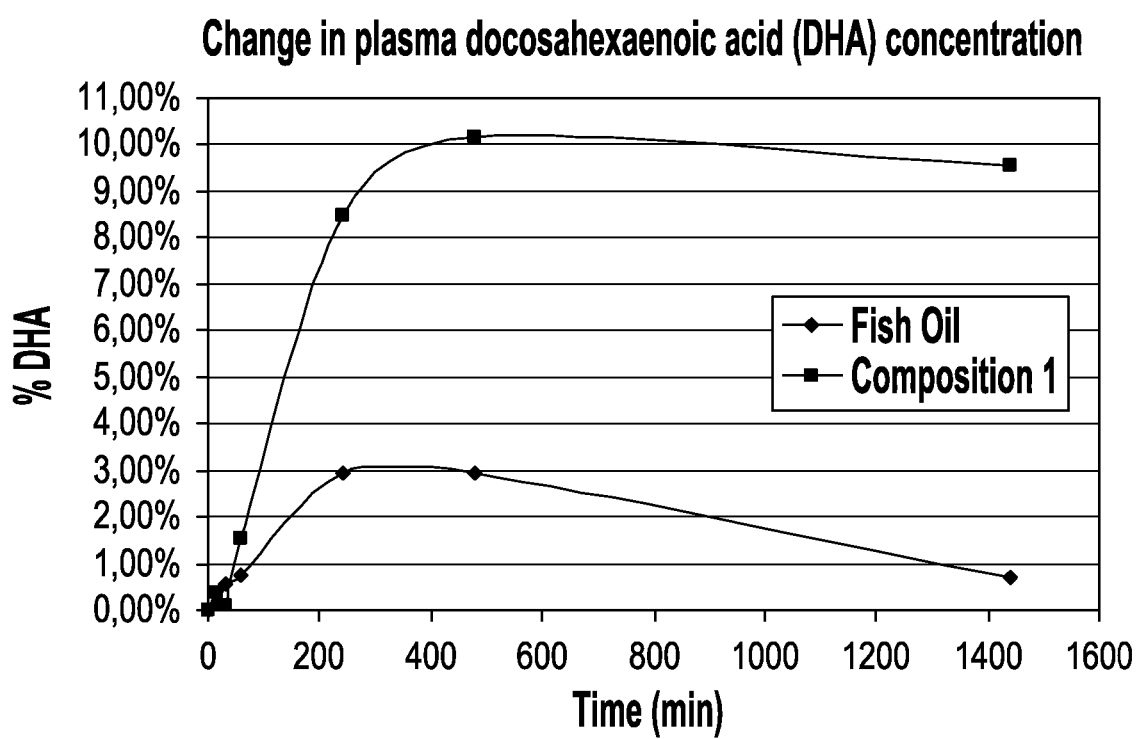
FIG. 11 represents a comparative in vivo absorption study of two different formulations containing docosahexaenoic acid (DHA) which are a fish oil and a composition according to another example.

FIG. 11 shows the change in plasma docosahexaenoic acid concentration of composition 1 compared to a fish oil upon time over a 1440 minutes study.

The relative bioavailability of docosahexaenoic acid from composition 1 compared to docosahexaenoic acid from fish oil is calculated with the formula:

$$\text{relative bioavailability} = \frac{[AUC]_A * \text{dose}_B}{[AUC]_B * \text{dose}_A}$$

The AUC (calculates area under the curve for concentration vs. time data) is calculated using linear trapezoidal rule. The use of the linear trapezoidal rule as a method for approximating the area under a concentration-time curve is widely accepted. In this experiment, the doses are the same. The calculated relative bioavailability of docosahexaenoic acid from composition 1 compared to a fish oil from time 0 to time 1440 min. is 4.48 and when the calculation is made from time 0 to infinity, the relative bioavailability is 50.31.

As it can be seen in FIG. 10, composition 1 permits to enhance the solubility of various active agents (bis-demethoxycurcumin, demetoxycurcumin, curcumin and total curcuminoids) in a lipid or lipid formulation. It can be clearly seen from FIG. 10 that such active agents have a greater solubility in a lipid formulation consisting of composition 1 than in a lipid formulation consisting of a fish oil. As it can be seen, the active agents are about 3 to 4 times more soluble in composition 1 than in a fish oil. It can thus also be seen the that such a composition is effective for solubilizing lipophilic active agents.

As it can be seen in FIG. 11, composition 1 permits to enhance the bioavailability of docosahexaenoic acid as compared to a fish oil. The relative bioavailability of docosahexaenoic acid from composition 1 compared to a fish oil calculated from time 0 to time 1440 min. is 4.48 and when the calculation is made from time 0 to infinity, the relative bioavailability of docosahexaenoic acid from composition 1 compared to a fish oil is 50.31. Such a study thus clearly shows that the compounds and compositions of the present disclosure are useful for enhancing bioavailability of an active agent.

EXAMPLE 6

The relative human bioavailability of two different compositions (composition 2 and a fish oil) containing docosahexaenoic acid (DHA) and omega-3 docosapentaenoic acid (DPAω3) has been determined.

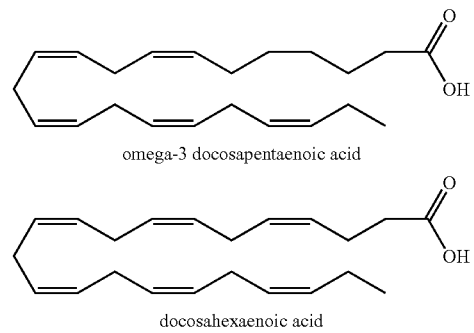

omega-3 docosapentaenoic acid docosahexaenoic acid

The fish oil comprises compounds 2 and 7 in about a 1:8 ratio (11% of 2 and 89% of 7):

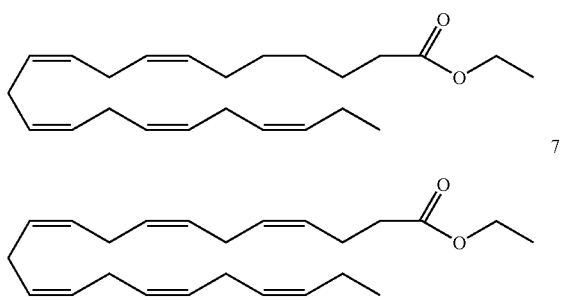

Composition 2 comprises compounds 1 and 5 and fish oil (comprising compounds 2 and 7 in about a 1:2 ratio. In other words, composition 2 comprises (about) compounds 1 (3.6%), 2 (7.4%), 5 (29.4%), and 7 (59.6%):

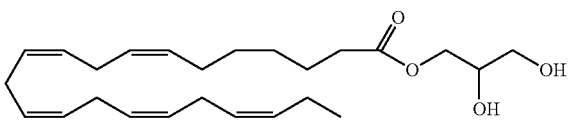

-continued

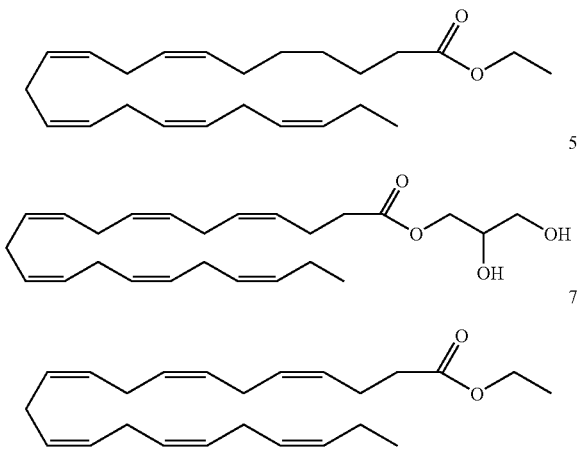

Composition 2 was prepared according to the same procedure as previously described in Example 2.

The relative human bioavailability of these two different compositions (composition 2 and a fish oil) was determined by a pilot cross-over study on one healthy volunteer (male). The volunteer fasted for 12 hours prior to the study. The participant consumed fish oil (capsules) equivalent to 3.0 g of DHA and 375 mg of DPAω3 as part of a breakfast. Controlled amount of boiled pasta was eaten after the 4 h time point. An initial blood sample (400 μl) was collected using a lancet at a fingertip into heparin tubes followed by samples at 1, 2, 3, 4, 5, 6, 7 and 8 hour after ingestion. Plasma was separated and immediately analysed for fatty acid composition. Fourteen days later (washout period), the procedure was repeated with composition 2 (capsules) equivalent to 3.0 g of DHA and 375 mg of DPA ω3.

Figure 12:
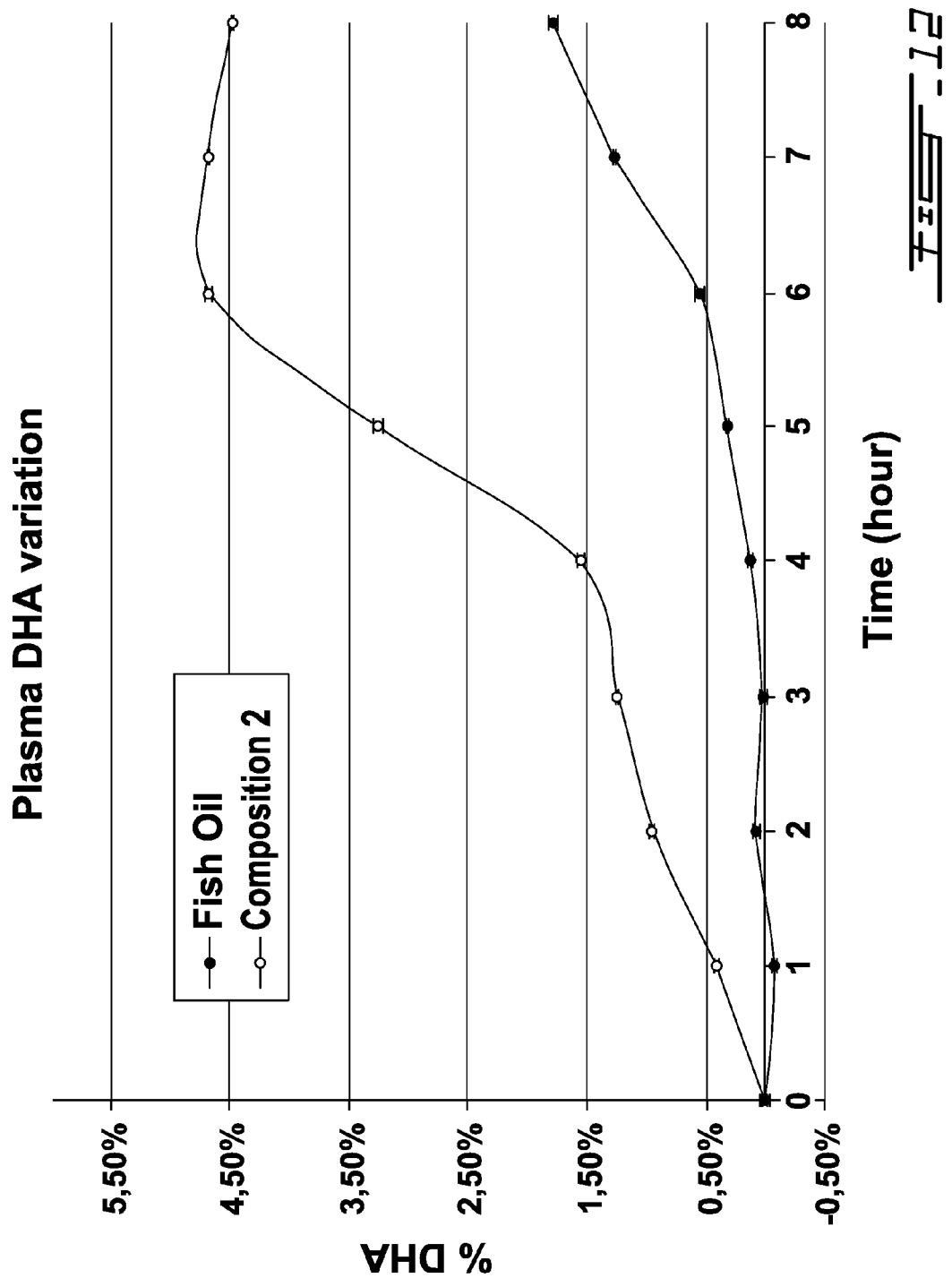
FIG. 12 represents a comparative human absorption cross-over study of two different compositions containing docosahexaenoic acid (DHA) which are a fish oil and a composition according to another example.
Figure 13:
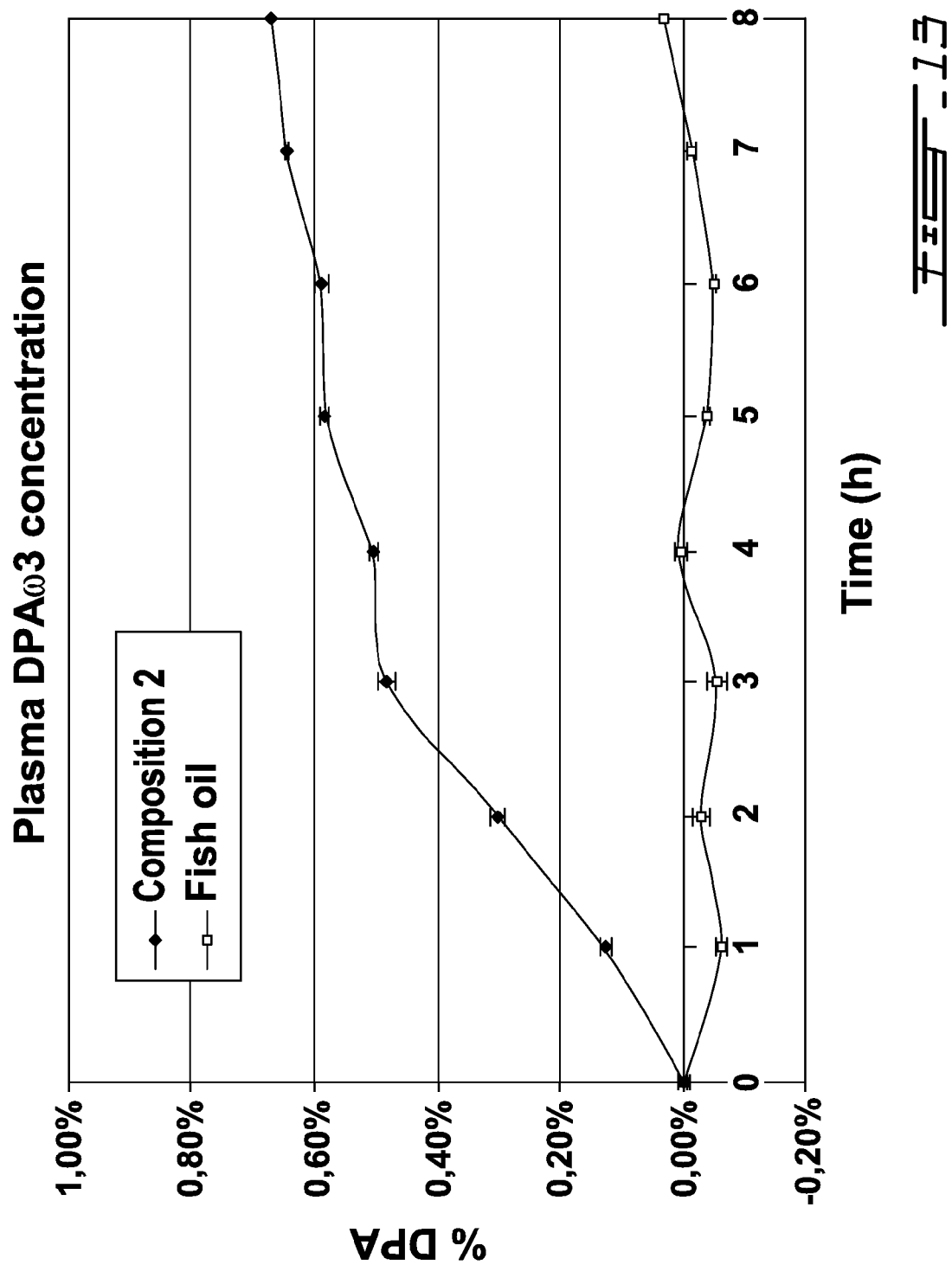
FIG. 13 represents a comparative human absorption cross-over study of two different compositions containing omega-3 docosapentaenoic acid (DPAω3) which are a fish oil and a composition according to another example.

The results of this study are shown in FIGS. 12 and 13.

FIG. 12 shows the change in plasma docosahexaenoic acid (DHA) concentration of composition 2 compared to fish oil upon time over an 8 hours study.

FIG. 13 shows the change in plasma omega-3 docosapentaenoic acid (DPAω3) concentration of composition 2 compared to fish oil upon time over an 8 hours study.

In FIG. 12 the proportion of DHA in plasma (% DHA) increased slowly only after 3 hours and reach a maximum of less than 2% after 8 hours when fish oil was taken alone. With composition 2, the DHA increased moderately right after the ingestion and after 4 hours the DHA increased rapidly to reach a plateau of more than 4.5% at 6 hours. After 8 hours the DHA variation is 4.5%.

In FIG. 13 the proportion of DPAω3 in plasma (% DPAω3) did not increase after 8 hours when fish oil was taken alone, this mean that DPAω3 was not absorbed in fish oil. With composition 2, the DPAω3 increased moderately right after the ingestion to reach a plateau of 0.5% at 3 hours. After 8 hours the DPAω3 variation was more than 0.6%

The relative bioavailability of fatty acids from composition 2 compared to fish oil is calculated with the formula:

$$\text{relative bioavailability} = \frac{[AUC]_A * \text{dose}_B}{[AUC]_B * \text{dose}_A}$$

The AUC (calculates area under the curve for concentration vs. time data) is calculated using linear trapezoidal rule. The use of the linear trapezoidal rule as a method for approximating the area under a concentration-time curve is widely accepted. In this experiment, the doses are the same. The calculated relative bioavailability of docosahexaenoic acid from composition 2 compared to fish oil from time 0 to infinity is 3.72. Thus, when DHA is in the presence of compounds 1 and/or 5, DHA is 3.72 times more bioavailable. For the relative bioavailability of DPAω3, no significant absorption was found with fish oil, compared to an increase of more than 0.6% after 8 hours with composition 2. The relative bioavailability of compound 1 and compound 5 is calculated with the same formula:

$$\text{relative bioavailability} = \frac{[AUC]_A * \text{dose}_B}{[AUC]_B * \text{dose}_A}$$

The calculated relative bioavailability of compound 1 compared to compound 5 from time 0 to infinity is 2.20. Thus, compound 1 is 2.2 times more bioavailable than compounds 5.

The compounds and compositions of the present disclosure can be used for enhancing bioavailability of an active agent. For example, the active agent can be a fatty acid or a derivative thereof (for example an ester of a fatty acid). For example, the compounds of the present disclosure can be used for enhancing bioavailability of at least one compound present in a fish oil. For example, the compounds of the present disclosure can be used for enhancing bioavailability of the ethyl ester of EPA and/or DHA.

EXAMPLE 7

Composition 3 (comprising compounds 1 and 5) at final concentration of 10 μg/ml, curcumin (5 μg/ml) and a 1:1 mixture of composition 3 (110 μg/ml) and curcumin (5 μg/ml) in DMSO (1%) was used for the in vitro assay. Composition 3 prepared according to the same procedure as previously described in Example 2)

The in vitro assay allows evaluation of the potential anti-inflammatory effects of compounds on the induced-release of pro-inflammatory mediator by monocyte cells. Typical human monocyte THP-1 cells, involved in inflammatory processes, are used in this assay. Measurement of pro-inflammatory mediator TNF-α is performed by ELISA (manufactured by R&D Systems) with artificial induction of pro-inflammatory agents by LPS (*E. Coli* 055:B5) during 4 hours. Known anti-inflammatory agent dexametazone was used as positive control.

Figure 14:
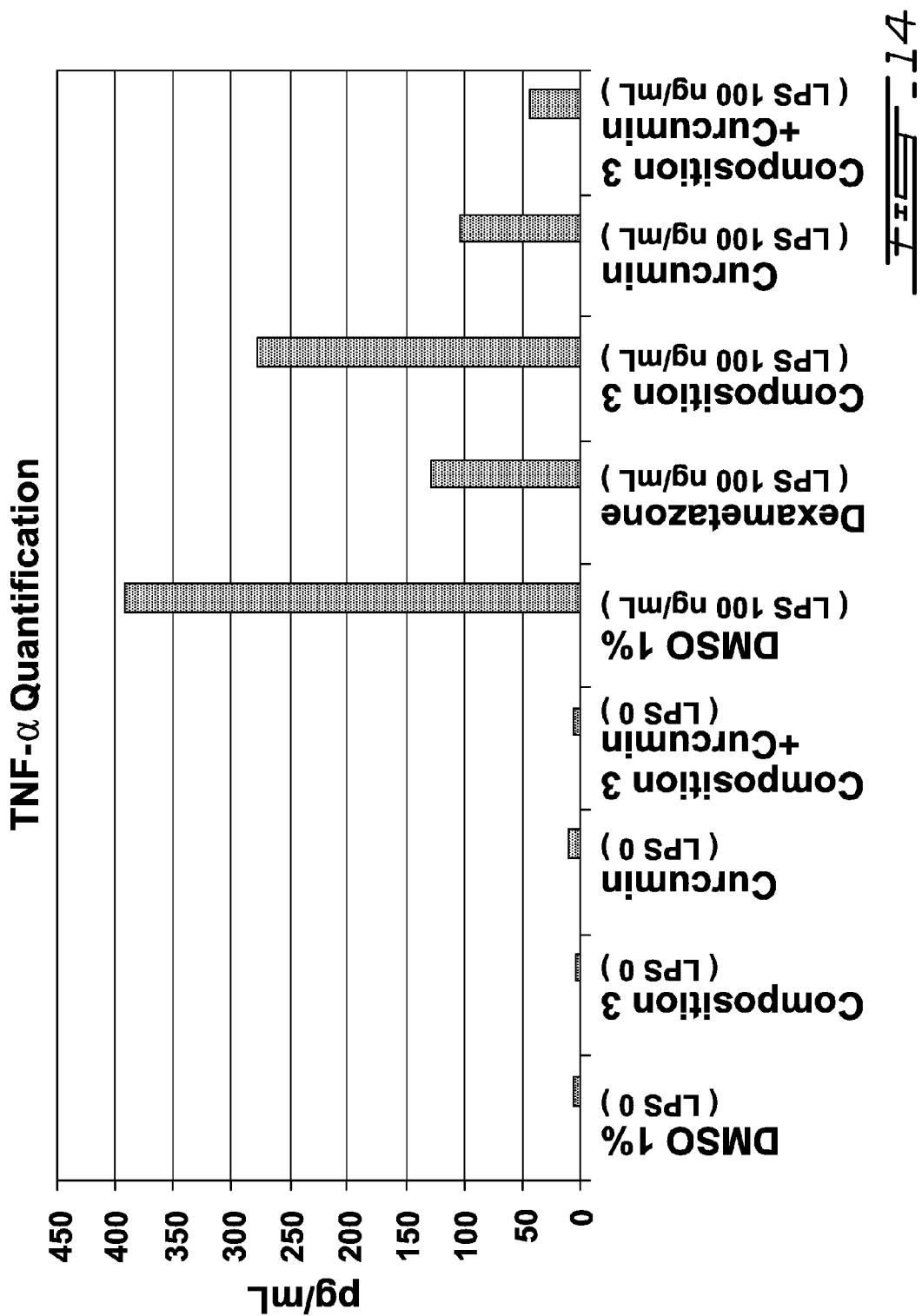
FIG. 14 represents an in vitro assay of a composition according to an example, wherein the assay was carried out on human THP-1 monocyte cell.

The results of this study are shown in FIG. 14.

In FIG. 14, no TNF-α was measured when no LPS is added to the monocyte THP-1 cells incubated with compounds or vehicle. With 100 ng/ml of LPS, 400 μg/ml of TNF-α was measured with the vehicle. With positive control dexametazone, only 125 μg/ml of TNF-α was measured, showing the anti-inflammatory effect of dexametazone. When composition 3 (10 μg/ml) was added, 275 μg/ml of TNF-α was measured and 100 μg/ml of TNF-α was measured when curcumin (5 μg/ml) is added. When a mixture of composition 3 and curcumin was added, less than 50 μg/ml of TNF-α was measured, showing a strong anti-inflammatory synergic effect.

While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present disclosure and including such departures from the present disclosure as come within known or customary practice within the art to which the present disclosure pertains and as may be applied to the features hereinbefore set forth, and as follows in the scope of the appended claims.

What is claimed is:
1. A composition comprising at least one compound chosen from compounds of formulae (I), (II), (III), and (IV):

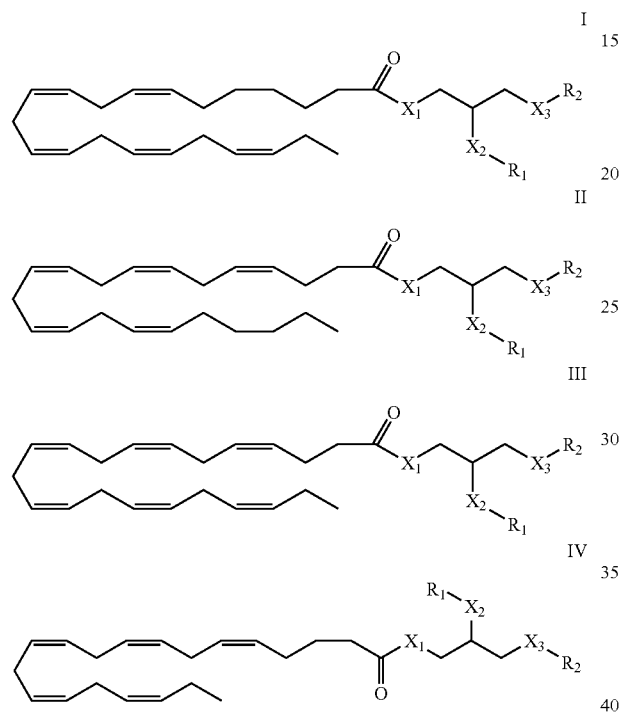

wherein
in formula (I):
X₁ is O, NH, or S;
X₂ is O, NH, or S;
X₃ is O, NH, or S;
R₁ and R₂ each independently represents —H, —C(O)NH₂, —S(O)NH₂, —S(O)₂NH₂, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH₂)ₙamino acid wherein the amino acid is connected through its alpha carbon atom, —(CH₂)ₙpeptide wherein the peptide is connected through the alpha carbon atom of one of its amino acids, —CH₂OR₅, —C(O)OR₅, —C(O)NR₅, —P(O)(OR₅)₂, —S(O)₂NHR₅, —SOR₅, —S(O)R₅, —arylP(O)(OR₅)₂, a sugar, or a sugar phosphate or R₁ and R₂ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;
R₅ is —H, —C₁-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one susbtituent chosen from —C1-C22 alkyl, —C2-C22 alkenyl, and —C2-C22 alkynyl, a —(CH₂)ₙamino acid wherein the amino acid is connected to the compound through its alpha carbon atom, a —(CH₂)ₙpeptide wherein the peptide is connected to the compound through the alpha carbon atom of one of its amino acids, a sugar or a sugar phosphate; and
n is an integer having a value of 0, 1, 2, 3, or 4,
in formula (II):
X₁ is O, NH, or S;
X₂ is O, NH, or S;
X₃ is O, NH, or S;
R₁ and R₂ each independently represents —H, —C(O)NH₂, —S(O)NH₂, —S(O)₂NH₂, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH₂)ₙamino acid wherein the amino acid is connected through its alpha carbon atom, —(CH₂)ₙpeptide wherein the peptide is connected through the alpha carbon atom of one of its amino acids, —CH₂OR₅, —C(O)OR₅, —C(O)NR₅, —P(O)(OR₅)₂, —S(O)₂NHR₅, —SOR₅, —S(O)₂R₅, -arylP(O)(OR₅)₂, a sugar, or a sugar phosphate or R₁ and R₂ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;
R₅ is —H, —C₁-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one susbtituent chosen from —C1-C22 alkyl, —C2-C22 alkenyl, and —C2-C22 alkynyl, a —(CH$_2$)$_n$amino acid wherein the amino acid is connected to the compound through its alpha carbon atom, a —(CH$_2$)$_n$peptide wherein the peptide is connected to the compound through the alpha carbon atom of one of its amino acids, a sugar or a sugar phosphate; and n is an integer having a value of 0, 1, 2, 3, or 4, in formula (III)

$X_1$ is O, NH, or S;
$X_2$ is O, NH, or S;
$X_3$ is O, NH, or S;
$R_1$ and $R_2$ each independently represents, —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$amino acid wherein the amino acid is connected through its alpha carbon atom, —(CH$_2$)$_n$peptide wherein the peptide is connected through the alpha carbon atom of one of its amino acids, —CH$_2$OR$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate, or $R_1$ and $R_2$ are joined together so as to form a five- to seven-membered non-aromatic heterocycle comprising at least one hetero atom chosen from nitrogen, oxygen, and sulfur, said heterocyle being unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

$R_5$ is —H, —C$_1$-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one susbtituent chosen from —C1-C22 alkyl, —C2-C22 alkenyl, and —C2-C22 alkynyl, a —(CH$_2$)$_n$amino acid wherein the amino acid is connected to the compound through its alpha carbon atom, a —(CH$_2$)$_n$peptide wherein the peptide is connected to the compound through the alpha carbon atom of one of its amino acids, a sugar or a sugar phosphate; and n is an integer having a value of 0, 1, 2, 3, or 4, in formula (IV)

$X_1$ is O, NH, or S;
$X_2$ is O, NH, or S;
$X_3$ is O, NH, or S;
$R_1$ and $R_2$ each independently represents, —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$amino acid wherein the amino acid is connected through its alpha carbon atom, —(CH$_2$)$_n$peptide wherein the peptide is connected through the alpha carbon atom of one of its amino acids, —CH$_2$OR$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate, or $R_1$ and $R_2$ are joined together so as to form a five- to seven-membered non-aromatic heterocycle comprising at least one hetero atom chosen from nitrogen, oxygen, and sulfur, said heterocyle being unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

$R_5$ is —H, —C$_1$-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one susbtituent chosen from —C1-C22 alkyl, —C2-C22 alkenyl, and —C2-C22 alkynyl, a —(CH$_2$)$_n$amino acid wherein the amino acid is connected to the compound through its alpha carbon atom, a —(CH$_2$)$_n$peptide wherein the peptide is connected to the compound through the alpha carbon atom of one of its amino acids, a sugar or a sugar phosphate; and n is an integer having a value of 0, 1, 2, 3, or 4, or a pharmaceutically acceptable salt thereof:

and at least one active agent chosen from a turmeric crude extract or purified extract from turmeric crude extract, curcumin, artemisinin, artemisia crude extract or purified extract from artemisia crude extract, green lipped mussels crude extract or purified extract from green lipped mussels crude extract, microalgae crude extract or purified extract of a microalgae, astaxanthin, lutein, zeaxanthin, and mixtures thereof.

2. The composition of claim 1, wherein said at least one active agent is chosen from a turmeric crude extract or purified extract from turmeric crude extract, curcumin, and mixtures thereof.

3. The composition of claim 2, wherein said at least one compound is chosen from:

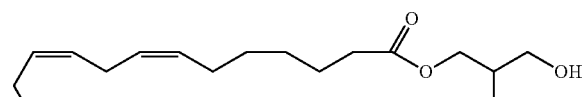

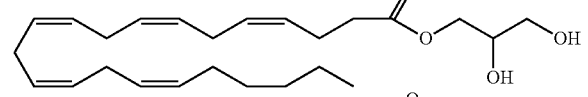

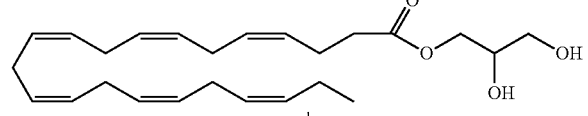

and

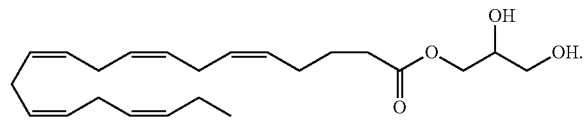

4. The composition of claim 2, wherein said at least one compound is chosen from:

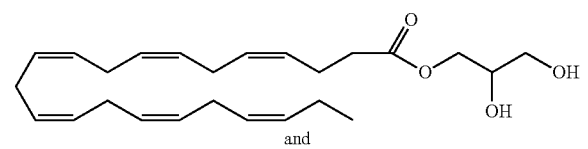

and

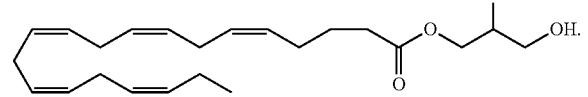

5. The composition of claim 2, wherein said at least one compound is chosen from:

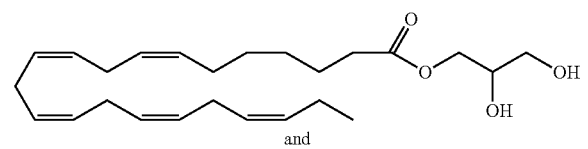

and

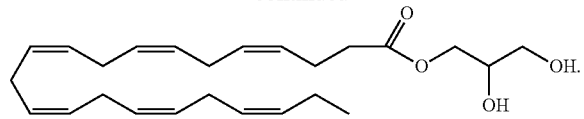

6. The composition of claim 1, wherein in formula (I):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (II):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (III):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl; —C1-C22 alkyl, —C1-C22 (hydroxy)alkyl, —C1-C22 (amino)alkyl, —C3-C22 alkenyl, or —C3-C22 alkynyl, in formula (IV):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

7. The composition of claim 2, wherein:

in formula (I):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (II):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (III):
  $X_1$ is O, NH, or S;
  $X_2$ is O, NH, or S;
  $X_3$ is O, NH, or S; and
  $R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (IV):
  $X_1$ is O, NH, or S;

$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

8. The composition of claim 1, wherein said at least one compound is chosen from compounds of formulae (III), and (IV), in which
in formula (III):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (IV):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

9. The composition of claim 2, wherein said at least one compound is chosen from compounds of formulae (III), and (IV), in which
in formula (III):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (IV):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

10. The composition of claim 1, wherein said at least one compound is a compound of formula (III), in which
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

11. The composition of claim 2, wherein said at least one compound is a compound of formula (III), in which
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

12. The composition of claim 1, wherein said at least one active agent is curcumin.

13. The composition of claim 1, wherein said at least one active agent is a turmeric crude extract or purified extract from turmeric crude extract.

14. The composition of claim 12, wherein said at least one compound is:

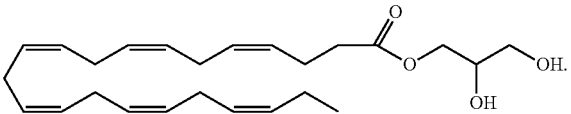

15. The composition of claim 12, wherein
in formula (I):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (II):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (III):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (IV):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl.

16. The composition of claim 13, wherein
in formula (I):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (II):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl,
in formula (III):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl; —C1-C22 alkyl, —C1-C22 (hydroxy)alkyl, —C1-C22 (amino) alkyl, —C3-C22 alkenyl, or —C3-C22 alkynyl, in formula (IV):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl.

17. The composition of claim 12, wherein said at least one compound is chosen from compounds of formulae (III), and (IV), in which in formula (III):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl, in formula (IV):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl.

18. The composition of claim 13, wherein said at least one compound is chosen from compounds of formulae (III), and (IV), in which in formula (III):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl, in formula (IV):
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl.

19. The composition of claim 12, wherein said at least one compound is a formula (III), in which
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl.

20. The composition of claim 13, wherein said at least one compound is a compound of formulae (III), in which
$X_1$ is O, NH, or S;
$X_2$ is O, NH, or S;
$X_3$ is O, NH, or S; and
$R_1$ and $R_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino) alkyl, —C3-C22 alkenyl, or —C3-C22 alkynyl.

21. The composition of claim 12, wherein said at least one compound is:

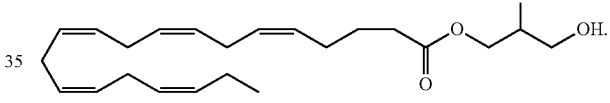

\* \* \* \* \*